(12) United States Patent
Ahearn et al.

(10) Patent No.: US 9,863,946 B2
(45) Date of Patent: Jan. 9, 2018

(54) CELL-BOUND COMPLEMENT ACTIVATION PRODUCTS AS DIAGNOSTIC BIOMARKERS FOR PRE-LUPUS

(71) Applicant: ALLEGHENY-SINGER RESEARCH INSTITUTE, Pittsburgh, PA (US)

(72) Inventors: Joseph M. Ahearn, Wexford, PA (US); Chau-Ching Liu, Pittsburgh, PA (US); Susan M. Manzi, Wexford, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 0 days.

(21) Appl. No.: 15/264,516

(22) Filed: Sep. 13, 2016

(65) Prior Publication Data

US 2017/0067893 A1 Mar. 9, 2017

Related U.S. Application Data

(63) Continuation-in-part of application No. 14/820,029, filed on Aug. 6, 2015, now Pat. No. 9,495,517, which is a continuation of application No. PCT/US2014/015032, filed on Feb. 6, 2014.

(60) Provisional application No. 61/762,620, filed on Feb. 8, 2013.

(51) Int. Cl.
| | |
|---|---|
| *C12Q 1/68* | (2006.01) |
| *G01N 33/53* | (2006.01) |
| *G01N 33/564* | (2006.01) |
| *G06F 19/00* | (2011.01) |
| *G01N 33/49* | (2006.01) |

(52) U.S. Cl.
CPC ......... *G01N 33/564* (2013.01); *C12Q 1/6883* (2013.01); *G01N 33/49* (2013.01); *G06F 19/322* (2013.01); *G06F 19/345* (2013.01); *G06F 19/3431* (2013.01); *C12Q 2600/112* (2013.01); *G01N 2333/4716* (2013.01); *G01N 2800/104* (2013.01); *G01N 2800/24* (2013.01)

(58) Field of Classification Search
None
See application file for complete search history.

(56) References Cited

U.S. PATENT DOCUMENTS

| | | |
|---|---|---|
| 7,390,631 B2 | 6/2008 | Ahearn et al. |
| 7,585,640 B2 | 9/2009 | Ahearn et al. |
| 7,588,905 B2 | 9/2009 | Ahearn et al. |
| 8,080,382 B2 | 12/2011 | Ahearn et al. |
| 8,126,654 B2 | 2/2012 | Ahearn et al. |
| 2005/0042602 A1 | 2/2005 | Ahearn et al. |
| 2010/0233752 A1 | 9/2010 | Ahearn et al. |
| 2012/0052066 A1 | 3/2012 | Calderon et al. |

FOREIGN PATENT DOCUMENTS

| | | |
|---|---|---|
| WO | WO-2010045611 A2 | 4/2010 |
| WO | WO-2011047337 A2 | 4/2011 |
| WO | WO-2012109592 A1 | 8/2012 |

OTHER PUBLICATIONS

"What is Lupus?" Lupus Education Series, Jan. 18, 2013; http://lupusny.org/news/foundation-news/2013/01/18/what-lupus-and-how-does-it-affect-body.*
Liu et al., "Cell-Bound Complement Biomarkers for Systemic Lupus Erythematosus: From Benchtop to Bedside", Rheum Dis Clin N Am, Feb. 1, 2010, vol. 36, pp. 161-172.
Pickering et al., "Links between complement abnormalities and systemic lupus erythematosus", Rheumatology, Jan. 1, 2000, vol. 39, pp. 133-141.
Ahearn et al., "Biomarkers for systemic lupus erythematosus", Translational Research, Feb. 10, 2012, vol. 159, pp. 326-342 (Abstract only).
Olsen NJ et al., "Biomarker-Driven Assessment of Lupus Progression", Sep. 18, 2012, printed from Internet, <http://www.lupus.org/research-news/entry/biomarker-driven-assessment-of-lupus-progress>... Jul. 20, 2015.
What is Lupus and How Does It Affect the Body? From 2012 Lupus Education Series, pp. 1-4, Jan. 18, 2013; http://lupusny.org/news/foundation-news/2013/01/18what-lupus-and-how-does-it-affect-body.
Vila L.M. et al., "Clinical outcome and predictors of disease evolution in patients with incomplete lupus erythematosus", Lupus, SAGE, GB, vol. 9, No. 2, Jan. 1, 2000, pp. 110-115.
Li Q.-Z. et al., "Interferon signature gene expression is correlated with autoantibody profiles in patients with incomplete lupus syndromes", Clinical and Experimental Immunology, vol. 159, No. 3, Mar. 1, 2010, pp. 281-291.
Kalunian Kenneth C. et al., "Measurement of Cell-Bound Complement Activation Products Enhances Diagnostic Performance in Systemic Lupus Erythematosus", Arthritis & Rheumatism, vol. 64, No. 12, Dec. 1, 2012, pp. 4040-4047.
Liu Chau-Ching et al., "Session Title: Systemic Lupus Erythematosus—Human Etiology and Pathogenesis Poster I Session Type: ACR Poster Session A Cell-Bound Complement Activation Products (CB-CAP) Profiles in Patients with Pre-Systemic Lupus Erythematosus", Sep. 29, 2015.
Manzi et al., "Measurement of Erythorcyte C4d and Complement Receptor 1 in Systemic Lupus Erythematosis", Arthritis Rheumatism, Nov. 2004, vol. 50, No. 11, p. 3596-3604.
Liu et al., Reticulocytes Bearing C4d as Biomarkers of Disease Activity for Systemic Lupus Erythematosus, Arthritis Rheumatism, vol. 52, No. 10, Oct. 2005, p. 3087-3099.

(Continued)

*Primary Examiner* — Michael Borin
(74) *Attorney, Agent, or Firm* — Fox Rothschild LLP

(57) ABSTRACT

Cell-bound complement activation product (CB-CAP) profiling and scoring serve as diagnostic biomarkers for patients to determine whether a patient who has not met at least four American College of Rheumatology (or similar e.g. SLICC) criteria for a definite Lupus diagnosis should be classified as exhibiting a pre-existing condition that this document refers to as pre-Lupus. This document also describes methods for determining whether a patient who has been determined to exhibit pre-Lupus has progressed to exhibiting definite Lupus.

8 Claims, 14 Drawing Sheets

(56) References Cited

OTHER PUBLICATIONS

Navratil et al., "Platelet-C4d is Highly Specific for Systemic Lupus Erythematosus", Arthritis Rheumatism, vol. 54, No. 2, Feb. 2006, p. 670-674.

Liu et al., "Lymphocyte-Bound Complement Activation Products as Biomarkers for Diagnosis of Systemic Lupus Erythematosus", Clinical Translational Science, vol. 2, Issue 4, p. 300-308, 2009.

* cited by examiner

| | E-C4d | R-C4d | P-C4d | T-C4d | B-C4d | M-C4d | G-C4d |
|---|---|---|---|---|---|---|---|
| SLE (n=429) | 7.58 (4.75-13.99) | 1.49 (0.75-3.82) | 0.71 (0.15-1.77) | 3.71 (1.60-12.78) | 25.68 (10.81-55.41) | 4.91 (3.11-10.07) | 1.52 (0.87-3.07)) |
| Pre-SLE (n=51) | 6.87 (3.93-13.29) | 1.39 (0.79-4.27) | 0.68 (0.24-1.84) | 2.45 (1.31-6.78) | 15.41 (8.84-35.21) | 4.96 (3.08-10.35) | 1.36 (0.72-2.28) |
| OD (n=285) | 4.48 (3.16-6.56) | 0.88 (0.51-1.65) | 0.40 (0.08-0.76) | 1.55 (0.99-2.38) | 9.88 (6.99-16.50) | 3.37 (2.09-5.05) | 0.99 (0.53-1.61) |
| HC (n=196) | 3.70 (2.63-5.22) | 0.80 (0.36-1.55) | 0.27 (0.00-0.58) | 1.24 (0.81-2.19) | 7.99 (5.31-10.84) | 3.86 (2.57-6.13) | 1.10 (0.74-1.64) |
| | | | | | | | |
| P value (SLE vs Pre-SLE) | 0.181 | 0.928 | 0.780 | 0.048 | 0.017 | 0.977 | 0.162 |
| P value (SLE vs OD) | <0.001 | <0.001 | <0.001 | <0.001 | <0.001 | <0.001 | <0.001 |
| P value (SLE vs HC) | <0.001 | <0.001 | <0.001 | <0.001 | <0.001 | <0.001 | <0.001 |
| P value (Pre-SLE vs OD) | <0.001 | 0.003 | 0.003 | <0.001 | 0.002 | <0.001 | <0.036 |

FIG. 7

CELL-BOUND COMPLEMENT ACTIVATION PRODUCTS AS DIAGNOSTIC BIOMARKERS FOR PRE-LUPUS

CROSS-REFERENCE TO RELATED APPLICATIONS

This application is a continuation-in-part of U.S. application Ser. No. 14/820,029, filed Aug. 6, 2015, which is a continuation of International Application Number PCT/US2014/015032, filed Feb. 6, 2014, which claims benefit of U.S. Provisional Patent Application No. 61/762,620, filed Feb. 8, 2013, the disclosures of each of which are hereby incorporated by reference herein, in their entireties.

STATEMENT OF FEDERALLY-SPONSORED RESEARCH

This invention was made with government support under grant number W81XWH-09-1-0275, awarded by the Department of Defense. This invention was made with government support under grant number R01 AI077591, awarded by the National Institutes of Health. This invention was made with government support under grant number R01 AR046588, awarded by the National Institutes of Health. The government has certain rights in the invention.

BACKGROUND

Systemic Lupus Erythematosus (SLE), commonly referred to as Lupus, is the prototypic autoimmune disease characterized by immune dysregulation (e.g., autoantibody and immune complex formation, complement activation, lymphocyte hyperreactivity, and skewed cytokine production) and consequent inflammatory tissue injury. The clinical manifestations of Lupus are heterogeneous, ranging from subtle symptoms to fatal disease, and may involve literally any tissue and organ of the patient. Although Lupus primarily affects women of reproductive age, it is a disease of any age and gender. The onset of Lupus may be insidious with symptoms such as fever, joint pain, and fatigue, which are common in non-Lupus diseases. Lupus is also characterized by periodic aggravation (flares) and remission of the disease. Meanwhile, serious organ damage may occur and go unrecognized since the early stage of the disease.

Diagnosing Lupus remains a major clinical challenge. Although several blood tests are commonly used to aid physicians in making a diagnosis of Lupus, no single test is sufficiently sensitive and specific for determining whether a patient has Lupus. The typical patient with Lupus requires four different physicians over a period of five years to be diagnosed in an accurate manner.

The non-specific symptoms and blood tests may sometimes be overlooked or overemphasized, resulting in under-diagnosis or overdiagnosis. Underdiagnosis and delayed diagnosis undoubtedly may lead to increased morbidity and mortality of patients who actually have Lupus. Conversely, overdiagnosis of Lupus may result in unnecessary exposure to toxic medications, which can be costly and have significant side effects in patients who do not have Lupus. Therefore, a timely and precise diagnosis has significant impact on not only the physical wellbeing of patients but also on the economic well being of the health care system.

This document describes methods and systems that may help solve at least some of the problems described above, and that may provide additional benefits.

SUMMARY

In an embodiment, this document discloses a method of determining whether to classify a patient as exhibiting pre-Lupus, comprising: receiving a blood sample for a patient who is determined to meet fewer than four classification criteria for Lupus; performing a panel of cell-bound complement activation product (CB-CAP) assays on the blood sample to generate a set of blood sampling data for the patient, wherein the set of blood sampling data comprises levels of at least two the following CB-CAPs for the patient: E-C4d, R-C4d, P-C4d, T-C4d, B-C4d, M-C4d, or G-C4d; comparing the CB-CAP levels for the patient with a set of control levels to determine a number of the CB-CAPs for which the patient's CB-CAP levels are elevated as compared to the control levels; generating a score based upon the number of the CB-CAPs for which the patient's CB-CAP levels exceed a threshold; determining whether the score is greater than an average score for other patients; and if the score is determined to be greater than an average score for the other patients, classifying the patient as not having Lupus but exhibiting an increased risk of developing Lupus, otherwise classifying the patient as neither having Lupus nor having the increased risk of developing Lupus.

In another embodiment, this document describes a method of classifying a subject as having either pre-Lupus or Lupus, which comprises, in a blood sample from the subject, identifying a subject who has been classified as exhibiting pre-Lupus; assaying a level of each of T-C4d and B-C4d in a blood sample for the subject; accessing a control data set, the control data set comprising a control level for each of T-C4d and B-C4d in a control blood sample obtained from the subject at an earlier time; comparing the levels of T-C4d and B-C4d in the blood sample with the control levels; if the levels of T-C4d and B-C4d in the blood sample as compared to the control levels have each increased by at least a threshold amount, classifying the subject as exhibiting Lupus; if the levels of T-C4d and B-C4d in the blood sample as compared to the control levels have not each increased by at least a threshold amount, classifying the subject as exhibiting pre-Lupus; and generating a report comprising an indication of whether the subject is classified as exhibiting Lupus or pre-Lupus.

In another embodiment, this document describes a system for determining whether to classify a patient as exhibiting pre-Lupus, comprising: a data storage facility holding a control data set of blood sampling data for a control subject population, wherein a first group of the subjects in the population are known to have Lupus and a second group of the subjects in the population are known to not have Lupus, and wherein the blood sampling data includes levels of cell-bound complement activation products (CB-CAPs) for each of the subjects; a processing device; and a computer-readable medium containing programming instructions that are configured to instruct the processing device to: identify a patient who meets fewer than four classification criteria for Lupus; receive a set of blood sampling data for the patient, wherein the set of blood sampling data comprises a plurality of CB-CAP levels for the patient, wherein the CB-CAP levels are for a panel of at least two of the following CB-CAPs: E-C4d, R-C4d, P-C4d, T-C4d, B-C4d, M-C4d, or G-C4d; compare the CB-CAP levels for the patient with the control levels to determine a number of the CB-CAPs for which the patient's levels are elevated as compared to the control levels; if the determined number of the CB-CAPs for which the patient's levels are elevated exceeds a threshold, classify the patient as not having Lupus but exhibiting an increased risk of developing Lupus, otherwise classify the patient as neither having Lupus nor having the increased risk of developing Lupus; and generate a report comprising an indication of whether the patient is classified as exhibiting the increased risk of developing Lupus.

BRIEF DESCRIPTION OF THE DRAWINGS

FIG. 7 illustrates the performance of 7 individual CB-CAP assays in pre-lupus vs. lupus vs. other autoimmune diseases vs. healthy controls (Median (25%-75%)).

DETAILED DESCRIPTION

Figure 1:
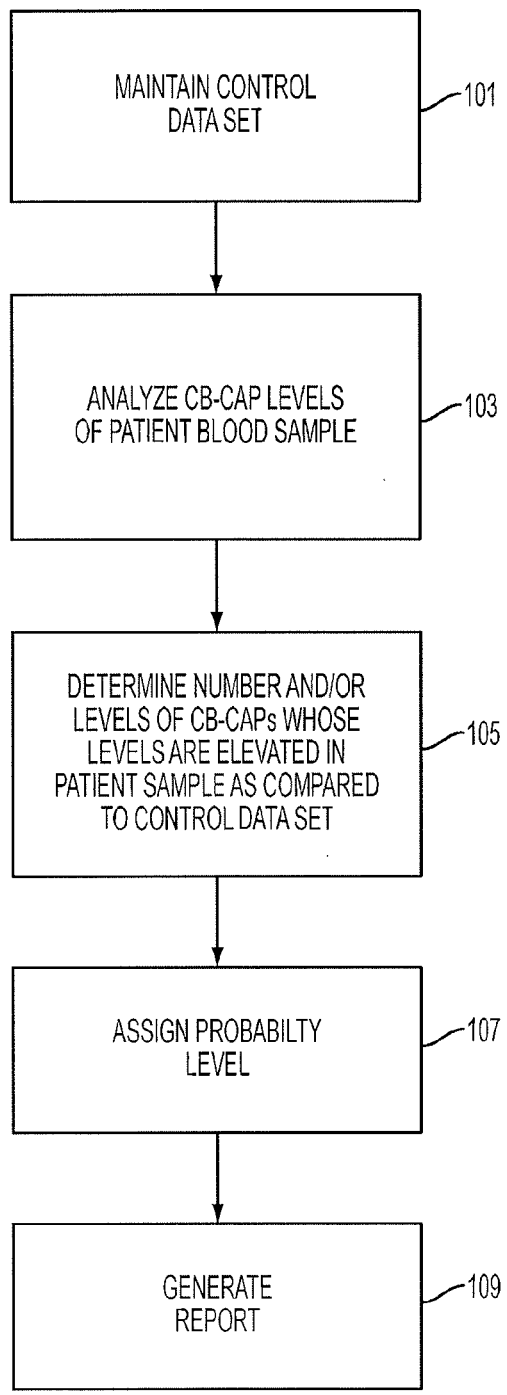
FIG. 1 is a flowchart describing a method of determining whether a patient should be classified as pre-Lupus.

This disclosure is not limited to the particular systems, devices and methods described, as these may vary. The terminology used in the description is for the purpose of describing the particular versions or embodiments only, and is not intended to limit the scope.

The following patent documents are incorporated by reference herein:

U.S. Pat. No. 8,126,654, issued to J. M. Ahearn and S. M. Manzi.

U.S. Pat. No. 8,080,382, issued to J. M. Ahearn and S. M. Manzi.

U.S. Pat. No. 7,585,640, issued to J. M. Ahearn et al.

U.S. Pat. No. 7,390,631, issued to J. M. Ahearn and S. M. Manzi.

U.S. Patent Application Publication No. 2010/0233752, naming J. M Ahearn, E. L. Erickson, D. M. Hawkins, S. M. Manzi, and T. Mercolino as inventors.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As used in this document, "Systemic Lupus Erythematosus", "SLE", or "Lupus" is a prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition and consequential activation of the complement system causes chronic inflammation and tissue damage. Lupus progresses in a series of flares, or periods of acute illness, followed by remissions. The symptoms of a Lupus flare, which vary considerably among patients and even within the same patient, include malaise, fever, joint pain, and photosensitivity (development of rashes after brief sun exposure). Other symptoms of Lupus include hair loss, ulcers of mucous membranes, inflammation of the lining of the heart and lungs which leads to chest pain, and synovitis, a painful inflammation of synovial membranes. Red blood cells, platelets and white blood cells can be targeted in Lupus, resulting in anemia, bleeding and thrombotic problems. More seriously, immune complex deposition and chronic inflammation in the glomerulus can lead to kidney involvement and occasionally failure requiring dialysis or kidney transplantation. Since the blood vessel is a major target of the autoimmune response in Lupus, premature strokes and heart disease are not uncommon. Over time, however, these flares can lead to irreversible organ damage. The term "Lupus" may also apply to other types of Lupus, such as Discoid Lupus Erythematosus or drug-induced Lupus.

As used in this document, the term "pre-Lupus" refers to a pre-existing condition that may serve as a preliminary indicator that a patient is at increased risk of developing Lupus. A patient diagnosed with pre-Lupus will have certain characteristics that would correspond to definite Lupus, but has not yet developed or been diagnosed with definite Lupus.

The pre-Lupus condition might be considered an equivalent of a precancerous or premalignant condition which is a state associated with a significantly increase risk of developing cancer or malignancy that should be treated accordingly. Examples of precancerous or premalignant states include colon polyps, associated with an increased risk of developing colon cancer, Barrett's esophagus, associated with an increased risk of developing esophageal cancer, cervical dysplasia, associated with an increased risk of developing cervical cancer, actinic keratosis, associated with an increased risk of developing skin cancer, and premalignant lesions of the breast, associated with an increased risk of developing breast cancer. In the majority of precancerous states, treatment of the lesion reduces or eliminates the risk of developing cancer. As such, early detection is essential. The pre-Lupus condition can be viewed in a similar context. Patients with pre-Lupus are at increased risk of developing definite lupus, however they may not. Early detection and appropriate treatment are essential to reducing the risk of disease progression.

Pre-Lupus is distinct from and should be distinguished from "Probable" Lupus. A diagnosis of probable Lupus is often rendered because the diagnosis of Lupus remains an art. There is no blood test or physical manifestation of the disease that can absolutely guarantee an accurate diagnosis of Lupus. Therefore, "probable Lupus" refers to the likelihood that a patient actually has definite Lupus at a given time. This is in contrast to "pre-Lupus", which indicates that a patient does not have definite Lupus at a given time but rather is at increased risk of eventually developing the disease although it is possible the patient will never do so.

As used in this document, a "complement pathway component" includes proteins from the classical, alternative, and lectin complement pathways, e.g., C1, C4, C2, C3 and fragments thereof, e.g., C4a, C4b, C2a, C2b, C4b, C2a, C3a, C3b, C4c, C4d, iC4b, C3d, C3i, C3dg. Also included are C5, C5b, C6, C7, C8, C9, C1inh, MASP1, MASP2, MBL, MAC, CR1, DAF, MCP, C4 binding protein (C4BP), Factor H, Factor B, C3bB, Factor D, Bb, Ba, C3bBb, properdin, C3bBb, CD59, C3aR, C5aR, C1qR, CR2, CR3, and CR4, as well as other complement pathway components, receptors and ligands not listed specifically herein.

As used herein, a "complement activation product" is a "complement pathway component" fragment as listed in the above paragraph, namely C4a, C4b, C2a, C2b, C4bC2a, C3a, C3b, C4c, C4d, iC4b, C3d, C3i, iC3b, C3c and C3dg.

A "cell-bound complement activation product" or "CB-CAP" is a combination of one or more complement activation products and a blood cell (such as but not limited to an erythrocyte, reticulocyte, T lymphocyte, B lymphocyte, monocyte, granulocyte or platelet) to which the complement activation product is bound.

As used in this document, a "control level" of any CB-CAP refers, in some embodiments, to a level of that CB-CAP obtained from the fluid sample of one or more individuals who do not suffer from the autoimmune, inflammatory or other disease or disorder that is of interest in the investigation. The level may be measured on an individual-by-individual basis, or on an aggregate basis such as an average. A control level can also be determined by analysis of a population of individuals who have the disease or disorder but are not experiencing an acute phase of the disease or disorder. In some embodiments, the control level of a respective CB-CAP is from the same individual for whom a diagnosis is sought or whose condition is being monitored, but is obtained at a different time. In certain embodiments, a "control" level can refer to a level obtained from the same patient at an earlier time, e.g., weeks, months, or years earlier.

As used in this document, "a difference from a control level" refers to a difference that is statistically significant, as determined by any statistical analysis method now or hereafter used by those in the art. A difference from a control level refers to a statistically significant difference between a control level of a respective CB-CAP and a level of the same CB-CAP from an individual for whom diagnosis or other information is sought, i.e., an experimental level. Those of skill will recognize that many methods are available to determine whether a difference is statistically significant and the particular method used is not limiting to the invention.

As used herein, the term "subject" is used to mean an animal, including, without limitation, a mammal. The mammal may be a human. The terms "subject" and "patient" may be used interchangeably.

For the purposes of this document, an "electronic device" or "processing device" refers to a device that includes a processor and a non-transitory, computer-readable memory. The memory may be integral to the device, or it may be remote from the device and accessible by the device via one or more communication networks. The memory may contain programming instructions that, when executed by the processor, are configured to cause the processor to perform one or more operations according to the programming instructions. Examples of electronic devices include computing devices, tablets, and smart phones.

This document describes methods and systems for CB-CAP profiling and scoring to serve as diagnostic biomarkers for determining that patients should be considered to be diagnosed as exhibiting pre-Lupus. This may enable a physician to render an earlier and more accurate diagnosis, prescribe earlier and more accurate therapeutic intervention, and ultimately reduce the risk of acute disease activity and long-term organ damage. This earlier and more accurate diagnosis and intervention may prevent previously-undiagnosed patients from progressing to definite Lupus, or at least delay such progression.

Lupus continues to pose both diagnostic and management challenges to physicians, in part due to the dearth of reliable tests and biomarkers. The current standard for diagnosing Lupus is a rheumatologist's judgment, based primarily on a standard classification scheme developed by the American College of Rheumatology (ACR). The ACR criteria are a set of clinical criteria that a medical professional may use to determine whether a patient has Lupus. A diagnosis of definite Lupus is made when a patient has met at least 4 of the 11 ACR criteria of clinical symptoms or laboratory tests. Because the various manifestations of Lupus may not manifest simultaneously, it often takes years before 4 criteria are met and a diagnosis is eventually made. Similar criteria have been adopted by the Systemic Lupus International Collaborating Clinics (SLICC).

To circumvent this dilemma, a class of patients who have met fewer than 4 ACR or SLICC criteria but nonetheless are suspected to have Lupus may be given a diagnosis of "pre-Lupus". However, there is no test currently available to measure the probability that such a patient actually has pre-Lupus, nor is there any agreed-upon test to reach even a diagnosis of potential Lupus other than by using the ACR or SLICC criteria. In addition, it is difficult to identify which patients who met fewer than 4 of the criteria should continue to be associated with a risk of developing Lupus, rather than being considered free from the disease. Some patients with pre-Lupus may go on to develop definite Lupus, potentially suffering from organ damage that might have occurred unnecessarily due to the missed opportunity of early treatment. Improving the timeliness and accuracy of diagnosis of Lupus would be greatly facilitated by the availability of biomarkers that can help identify patients who have "pre-Lupus" and will benefit from early management of preventable organ damage.

Numerous studies have indicated a prominent role of the complement system in the pathogenesis of Lupus. Because complement proteins are abundantly present in the circulation and can readily interact with circulating cells, the inventors have hypothesized that complement activation products bound to circulating cells may serve as more informative Lupus biomarkers than soluble complement proteins. Indeed, significant levels of complement C4-derived activation products, particularly C4d, are present specifically on the surfaces of erythrocytes, reticulocytes, platelets, and lymphocytes of patients with Lupus. These cell-bound complement activation products (CB-CAPs) can serve as unique biomarkers not only for diagnosis but also for monitoring disease activity in patients with Lupus.

As described in this document, the inventors have surprisingly found that complement activation products are capable of binding to essentially all circulating blood cells and, upon binding, may alter the functions of these cells, thereby contributing to a wide range of immunopathogenic responses in Lupus. In this context, a method and system that profiles the CB-CAP patterns in patients at risk for developing Lupus may provide a "window" to look into a pathogenic process that evolves from "pre-Lupus" to definite Lupus. Therefore, profiling CB-CAP patterns may allow physicians to determine whether to diagnose a patient as exhibiting a pre-Lupus condition. This may help identify patients who are at an increased risk of developing Lupus, and institute appropriate prophylactic and treatment measures accordingly with the intention of delaying or preventing development of Lupus or minimizing manifestations of the disease.

An overview of this process is described in FIG. 1, which illustrates a process whereby a baseline data set is maintained in a computer-readable memory 101. The control data set contains sampling data for a set of patients who have been confirmed as not having Lupus. The sampling data includes data from blood samples taken from each patient, where the data identifies a level of one or more CB-CAPs in each patient's blood sample, such as the CB-CAPs listed in the next paragraph.

The control data set may include measurements of control levels for various CB-CAPs, which may include the complement activation products C4d or C3d bound to any or all of the following cell types: erythrocytes (with the CB-CAPs represented as E-C4d, E-C3d), reticulocytes (with the CB-CAPs represented as R-C4d, R-C3d), T lymphocytes (with the CB-CAPs represented as T-C4d, T-C3d), B lymphocytes (with the CB-CAPs represented as B-C4d, B-C3d), monocytes (with the CB-CAPs represented as M-C4d, M-C3d), and granulocytes (with the CB-CAPs represented as G-C4d, G-C3d). The CB-CAPs also may include C4d on platelets [P-C4d] as well as complement receptor 1 (CR1) expressed on erythrocytes [E-CR1]. In addition to the 13 CB-CAPs listed above, other CB-CAP control levels such as but not limited to those present on basophils, eosinophils, circulating endothelial cells also may be stored in the data set.

This system may help determine whether a patient should be classified as having a pre-Lupus condition, and thus be a candidate for additional testing or treatment. When a blood sample is taken from a patient for whom a diagnosis is desired, the sample will be analyzed for the levels of any or all of the CB-CAPs for which levels are also available in the data set 103. The sampling data may be entered into or received by a processing device, which will compare the CB-CAP levels from the patient's sample with the CB-CAP levels in the data set to determine a number and/or levels 105 of CB-CAPs for which the patient exhibits an elevated level. A level of a CB-CAP in the patient's sample may be determined as "elevated" if it exhibits a difference from (above) a control level of the same CB-CAP in the control set. As an example, if the level of the CB-CAP in the patient's sample is at least two standard deviations above the level of the same CB-CAP in the control set, the level may be considered to be elevated. Other methods of determining statistical significance may be used to determine whether the level is elevated.

Based on the determined number of ACR criteria (or SLICC criteria or other criteria) for classification of Lupus met by a given patient (fewer than four) and based on the determined number of elevated CB-CAPs that are present in the patient, and/or a measure of the level of elevation of each elevated CB-CAP, the system may assign a probability level to the patient 107. A probability level is a percentage, a score, or some other indicia that a medical professional may use to determine whether the patient is likely to have pre-Lupus. In this document, a probability level may refer to a measure of a probability that a patient has pre-Lupus. The probability level may be determined as a factor of the number of abnormal (elevated) CB-CAPs that exist in the set. The probability level may be as simple as the percentage of CB-CAPs that are elevated (e.g., 40% if two out of five CB-CAPs are elevated). Or, it may be adjusted by any number of factors. For example, individual CB-CAPs may be weighted so that some CB-CAPs will contribute to a higher probability level if elevated than others will contribute. The calculation also may include variables such as the extent to which one or more of the CB-CAPs are elevated, and/or one or more classification criteria, such as ACR or SLICC criteria.

When assigning the probability level and determining whether the patient should be classified as exhibiting pre-Lupus, the system may not merely look at a single CB-CAP, but instead it may require a combination of several CB-CAPs to be elevated by at least a threshold amount before the system will classify the patient as pre-Lupus. In an embodiment, the system may look at any number of CB-CAPs and require that at least eight of the CB-CAPs in the patient be elevated as compared to the control set in order to classify the patient as pre-Lupus. In some embodiments, the CB-CAP panel may include more than eight tests. In some embodiments, the probability of being diagnosed as having pre-Lupus increases as the number of abnormal tests in the panel increases. In addition, in some embodiments, the system also may determine whether the patient is exhibiting a decreased level of E-CR1 as compared to the E-CR1 levels of the control set, and it may classifying the patient as exhibiting pre-Lupus only if the patient also exhibiting a decreased level of E-CR1 as compared to E-CR1 control levels in the control data set.

In other embodiments, it may be advantageous and/or necessary to perform a more limited panel of CB-CAP assays to determine if a patient can be classified as having pre-lupus.

The system may then generate a report 109 with a diagnosis, such as the probability level itself, or one or more narrative or graphic indicia that describes the reasons why the patient is considered to exhibit (or not exhibit) pre-Lupus. The report will provide an assessment of whether the patient could be classified as a pre-Lupus patient. The system may be remote from that of a patient or medical professional, and some or all of the elements of the system may be present in multiple systems, such as a cloud-based system where the control data set is remote from the system that performs the processing and analysis, but connected via one or more communication networks.

Figure 4:
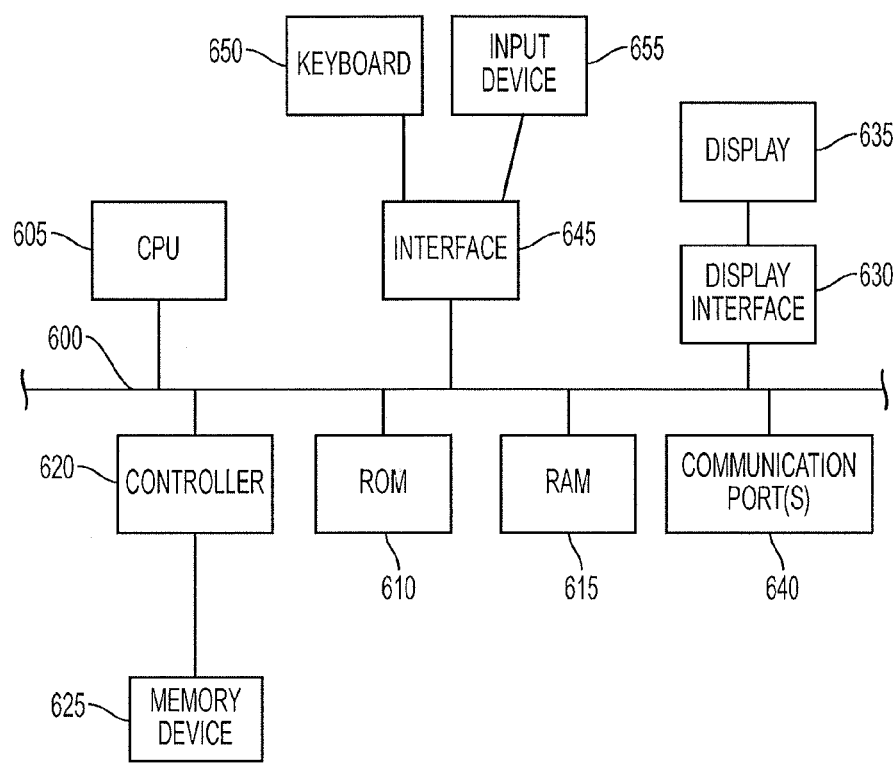
FIG. 4 is a block diagram illustrating various hardware that may be included in an electronic device that implements various processes described in this document.

FIG. 4 depicts an example of internal hardware that may be used to contain or implement the various computer processes and systems as discussed above. An electrical bus 600 serves as the main information highway interconnecting the other illustrated components of the hardware. CPU 605 is the central processing unit of the system, performing calculations and logic operations required to execute a program. CPU 605, alone or in conjunction with one or more of the other elements disclosed in FIG. 4, is a processing device, computing device or processor as such terms are used within this disclosure. Read only memory (ROM) 610 and random access memory (RAM) 615 constitute examples of memory devices. The processing device may execute programming instructions stored on a memory device to perform the methods disclosed in this document. When this document uses the term "processor" or "processing device," it is intended to include a single device or any number of devices that collectively perform a process, unless specifically stated otherwise.

A controller 620 interfaces with one or more optional memory devices 625 that service as date storage facilities to the system bus 600. These memory devices 625 may include, for example, an external DVD drive or CD ROM drive, a hard drive, flash memory, a USB drive or another type of device that serves as a data storage facility. As indicated previously, these various drives and controllers are optional devices. Additionally, the memory devices 625 may be configured to include individual files for storing any software modules or instructions, auxiliary data, incident data, common files for storing groups of contingency tables and/or regression models, or one or more databases for storing the information as discussed above.

Program instructions, software or interactive modules for performing any of the functional steps associated with the processes as described above may be stored in the ROM 610 and/or the RAM 615. Optionally, the program instructions may be stored on a tangible computer readable medium such as a compact disk, a digital disk, flash memory, a memory card, a USB drive, an optical disc storage medium, and/or other recording medium.

A display interface 630 may permit information from the bus 600 to be displayed on the display 635 in audio, visual, graphic or alphanumeric format. Communication with external devices may occur using various communication ports 640. A communication port 640 may be attached to a communications network, such as the Internet, a local area network or a cellular telephone data network.

The hardware may also include an interface 645 which allows for receipt of data from input devices such as a keyboard 650 or other input device 655 such as a remote control, a pointing device, a video input device and/or an audio input device.

Figure 5:
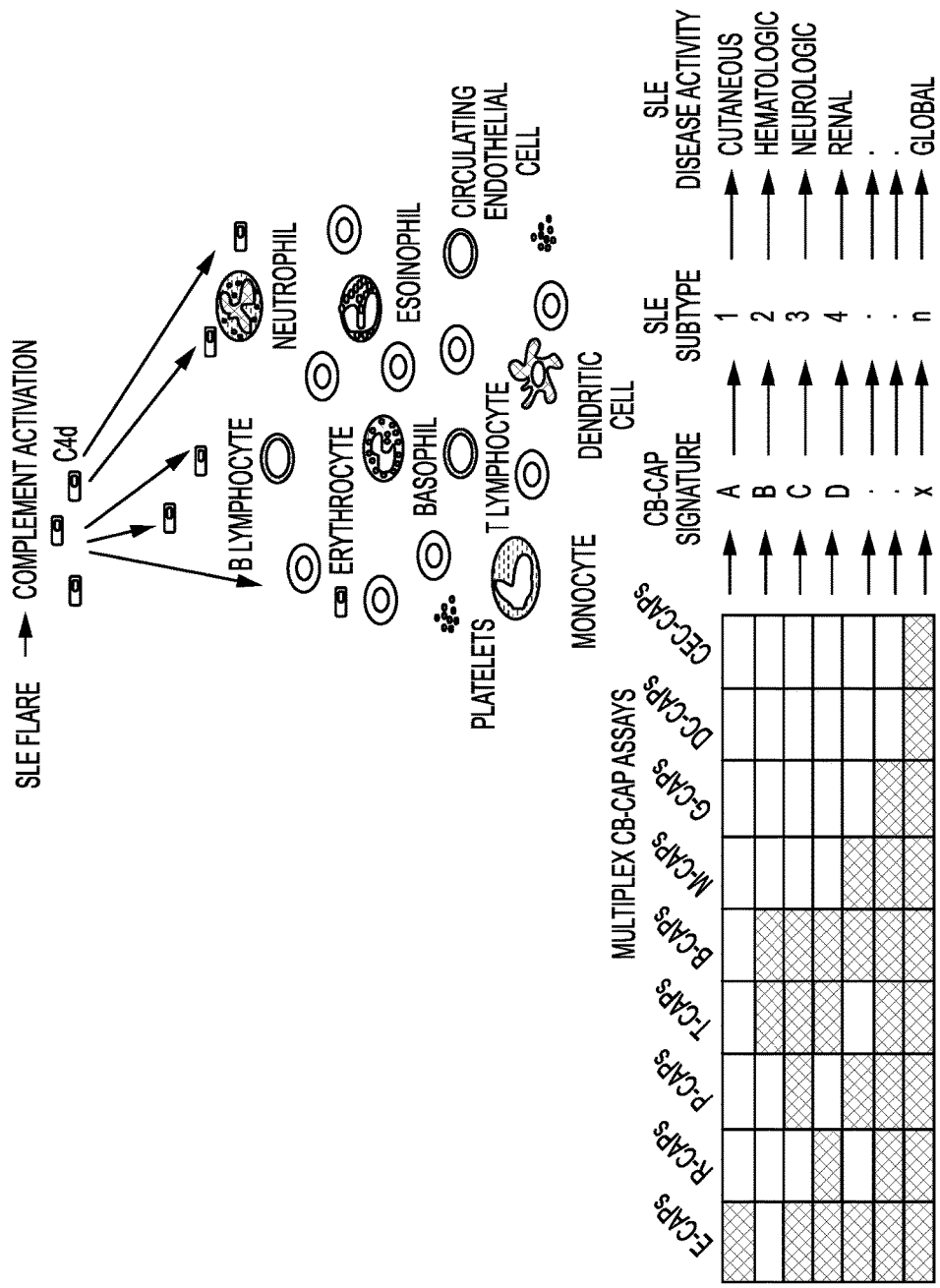
FIG. 5 illustrates a conceptual presentation of the CB-CAP signature.
Figure 6:
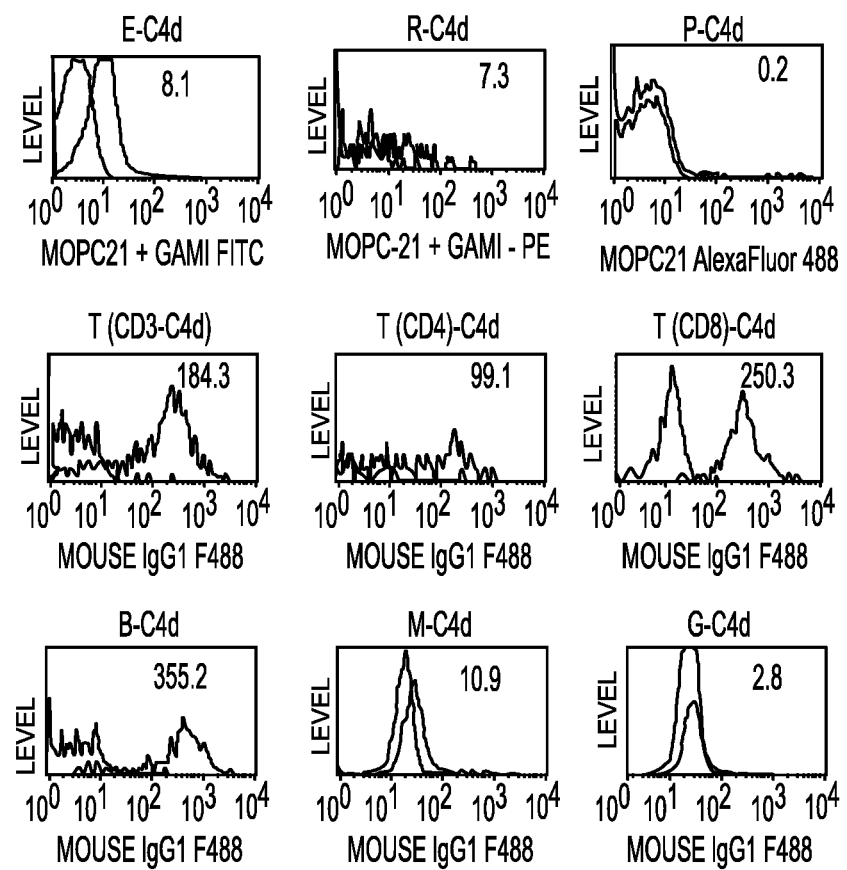
FIG. 6 illustrates a lupus patient CB-CAP signature.

The present inventors have determined that an individual with lupus or pre-lupus generates a distinct CB-CAP signature, as depicted in FIG. 5. The pattern of CB-CAP positive assays in a given individual is distinct, cannot be predicted, and can be used for classification/diagnosis, monitoring, stratification, and as companion diagnostics to predict response to and/or titrate therapies. An example of a patient-specific CB-CAP signature is demonstrated in FIG. 6 for patient #101601 who suffers from definite systemic lupus erythematosus. The signature of this patient includes abnormal elevations of levels of R-C4d, T(CD3)-C4d, T(CD4)-C4d, T(CD8)-C4d, B-C4d, and M-C4d, however values for the other CB-CAP assays, including E-C4d, P-C4d and G-C4d, were not within the lupus/pre-lupus range. Other individuals have their own unique signatures (data not shown). As such, it may be advantageous in some patients to focus on those CB-CAPs that are positive, rather than on the entire panel, for purposes of longitudinal observation, classification, monitoring, stratification and predicting response to therapy.

Additionally, it may be advantageous to use smaller CB-CAP assay panels in situations in which an individual patient may not have sufficient cells of a certain lineage (erythroid, myeloid, megakaryocyte) or lineage subset (T cell, B cell, etc.) to generate a meaningful CB-CAP value for that particular cell type/assay. This may be due to targeted cellular depletion therapy (e.g., Rituximab depletion of B lymphocytes) or due to the pathogenesis of the disease lupus, pre-lupus, or other condition that either destroys or suppresses maturation of certain cell populations leading to anemia (erythroid), leukopenia (myeloid), thrombocytopenia (megakaryocytic). Immune-mediated attack of specific cells such as in hemolytic anemia and immune-mediated thrombocytopenia may also confound interpretation of E-C4d, R-C4d and P-C4d assays. In these cases and potentially others, it may be advantageous and perhaps necessary to perform a limited and selected panel of CB-CAP assays for patients with pre-lupus to classify, monitor, stratify, and/or predict responses to therapy.

In embodiments, CB-CAP levels may be determined by any suitable method. Such assays for CB-CAPs may include, but are not limited to, enzyme-linked immunoassays and use of polyclonal antibodies. In embodiments, monoclonal antibodies may be used.

In embodiments, a method is provided for determining whether to classify a patient as exhibiting pre-Lupus, comprising: receiving a blood sample for a patient who is determined to meet fewer than four classification criteria for Lupus; performing a panel of cell-bound complement activation product (CB-CAP) assays on the blood sample to generate a set of blood sampling data for the patient, wherein the set of blood sampling data comprises levels of at least two, at least three, at least four, at least five, at least six, or all seven of the following CB-CAPs for the patient: E-C4d, R-C4d, P-C4d, T-C4d, B-C4d, M-C4d, and G-C4d; and, optionally by a processing device, comparing the CB-CAP levels for the patient with a set of control levels to determine a number of the CB-CAPs for which the patient's CB-CAP levels are elevated as compared to the control levels, generating a score based upon the number of the CB-CAPs for which the patient's CB-CAP level exceeds a threshold, determining whether the score is greater than an average score for other patients; and if the score is determined to be greater than an average score for the other patients, classifying the patient as not having Lupus but exhibiting an increased risk of developing Lupus, otherwise classifying the patient as neither having Lupus nor having the increased risk of developing Lupus. In embodiments, the other patients may be healthy controls. In embodiments, the other patients may be patients with immune and/or inflammatory diseases that are not Lupus.

In embodiments, a report may be generated comprising an indication of whether the subject is classified as exhibiting an increased risk of developing Lupus.

In various embodiments described in this document, a "score" relating to CB-CAP levels associated with a patient may be derived in any useful manner. In embodiments, a "score" may be based upon the number of the CB-CAPs for which the patient's CB-CAP level exceeds a threshold, as described above. In other embodiments, a "score" may be some function of that number.

In embodiments, a system is provided for determining whether to classify a patient as exhibiting pre-Lupus, comprising: a data storage facility holding a control data set of blood sampling data for a control subject population, wherein a first group of the subjects in the population are known to have Lupus and a second group of the subjects in the population are known to not have Lupus, and wherein the blood sampling data includes levels of cell-bound complement activation products (CB-CAPs) for each of the subjects; a processing device; and a computer-readable medium containing programming instructions that are configured to instruct the processing device to: identify a patient who meets fewer than four classification criteria for Lupus; receive a set of blood sampling data for a patient, wherein the set of blood sampling data comprises a plurality of CB-CAP levels for the patient, wherein the CB-CAP levels are for a panel of at least two, at least three, at least four, at least five, at least six, or all seven of the following CB-CAPs: E-C4d, R-C4d, P-C4d, T-C4d, B-C4d, M-C4d, and G-C4d; compare the CB-CAP levels for the patient with the control levels to determine a number of the CB-CAPs for which the patient's levels are elevated as compared to the control levels; if the determined number of the CB-CAPs for which the patient's levels are elevated exceeds a threshold, classify the patient as not having Lupus but as exhibiting an increased risk of developing Lupus, otherwise classify the patient as neither having Lupus nor having the increased risk of developing Lupus. A report may be generated comprising an indication of whether the patient is classified as exhibiting the increased risk of developing Lupus.

Optionally, a method or system may include selecting the CB-CAPS for which to perform assays by assessing one or more additional characteristics of the patient. For example, in one embodiment, the method may include analyzing blood cells of a patient to determine whether the patient includes cells of a particular lineage (e.g., erythroid, myeloid, megakaryocyte) or lineage subset (e.g., T-cells, B-cells, etc) that exceed a percentage threshold, and only performing assays on those lineages or lineage subsets that exceed the percentage threshold. For example, if the patient's blood sample includes less than 1% T-cells, B-cells, or another lineage subset, then assays may not be performed on CP-CAPs that correspond to that lineage subset (e.g., T-C4d and T-C3d, or B-C4C and B-C3d).

In embodiments, a method is provided for classifying a subject as having either pre-Lupus or Lupus, which comprises, in a blood sample from the subject:

assaying a level of each of T-C4d and B-C4d; and, optionally by a processing device:

accessing a control data set, the control data set comprising a control level for each of T-C4d and B-C4d, comparing the levels of T-C4d and B-C4d in the blood sample from the subject with the control levels, if the levels of T-C4d and B-C4d in the subjects's sample as compared to the control levels exceeds a threshold, classifying the subject as exhibiting Lupus, and if the levels of T-C4d and B-C4d in the subject's sample as compared to the control levels are below a threshold, classifying the subject as exhibiting an increased risk of developing Lupus. A report may be generated comprising an indication of whether the subject is classified as exhibiting Lupus or the increased risk of developing Lupus.

In embodiments, a method is provided for monitoring the progression of pre-Lupus to Lupus in a subject who has been classified as exhibiting pre-Lupus, which comprises: in a blood sample from the subject, assaying a level of each of T-C4d and B-C4d; and, optionally by a processing device: accessing a control data set, the control data set comprising a level of each of T-C4d and B-C4d in a control blood sample obtained from the same subject at an earlier time, comparing the level of each of T-C4d and BC4d in the blood sample from the subject with the levels of each of T-C4d and B-C4d in the control blood sample obtained from the same subject at an earlier time, and if the levels of T-C4d and B-C4d in the sample each increased by at least a threshold amount as compared to the control sample, classifying the disease state of the subject as having progressed from pre-Lupus to Lupus. A report may be generated comprising an indication of whether the subject is classified as having progressed to exhibiting Lupus.

The following examples serve to further illustrate various embodiments.

EXAMPLES

Example 1

CB-CAP assays were performed on blood samples obtained from patients given a diagnosis of "pre-Lupus" by lupologists, rheumatologists with particular expertise in the diagnosis and care of patients with Lupus. Four hundred and forty-seven patients who met the ACR 1982 or 1997 revised classification criteria for definite Lupus (≥4 criteria) were included in the data set. Twenty-four patients who presented SLE-related symptoms but nevertheless did not meet the definite Lupus criteria (i.e., they exhibited less than four of the ACR criteria) were diagnosed as "pre-Lupus" by expert Lupus diagnosticians because they presented Lupus-related symptoms, were not considered to have another disease, were not considered to have undifferentiated connective tissue disease, and were not considered to have an overlap of more than one disease. Their disease was considered to be Lupus-like but with insufficient number of the ACR criteria to be diagnosed as definite Lupus. These patients were diagnosed as "pre-Lupus" suggesting that a Lupus-like disease process was present that may or may not develop into definite Lupus however they are at increased risk of developing definite Lupus. This increased risk is based upon the known time course by which Lupus develops. In the majority of patients, criteria become positive during chronological evolution of the disease such that most patients with Lupus will have had only 1, 2 or 3 criteria present before developing the fourth criterion that permits definite diagnosis. The ability to diagnose pre-Lupus would enable earlier treatment and preventive measures to reduce disease damage over time.

Two hundred and eighty-six patients with non-Lupus immune-inflammatory diseases were recruited during the same period of time. These patients included 41 patients with Sjogren's syndrome, 20 patients with rheumatoid arthritis, 7 patients with scleroderma, 15 patients with antiphospholipid syndrome, 11 patients with idiopathic inflammatory myopathy, 8 patients with vasculitis, 5 patients with inflammatory bowel disease, 4 patients with primary Raynaud's phenomenon, 4 patients with discoid or cutaneous Lupus, 3 patients with psoriasis, 3 patients with Wegener's granulomatosis, 1 patient with Bechet's disease, 1 patient with sarcoidosis, 5 patients with various infections, and 192 patients with undifferentiated connective tissue disease or unclear disorders at the time of the visit.

In addition, one hundred and ninety-six healthy individuals were recruited as normal controls. To confirm their healthy status, those participants completed a brief questionnaire regarding existing medical conditions.

Flow Cytometric Assays for CB-CAP Profiling: For each participant, a 3-ml sample of blood was collected into a Vacutainer tube containing EDTA as an anticoagulant (Becton Dickinson, Franklin Lakes, N.J.). Blood samples were stored at 4° C. and analyzed within 24 hours after collection. Each blood sample was analyzed for a total of thirteen CB-CAPs (C4d and C3d on 6 cell types—erythrocytes [E-C4d, E-C3d], reticulocytes [R-C4d, R-C3d], T lymphocytes [T-C4d, T-C3d], B lymphocytes [B-C4d, B-C3d], monocytes [M-C4d, M-C3d], and granulocytes [G-C4d, G-C3d], and C4d on platelets [P-C4d]) as well as complement receptor 1 (CR1) expressed on erythrocytes [E-CR1]). Levels of C4d and C3d bound to erythrocytes, reticulocytes, and platelets as well as levels of E-CR1 were measured following previously published protocols. [Manzi S, et al., Measurement of erythrocyte C4d and complement receptor 1 in systemic lupus erythematosis. Arthritis Rheum. 2004; 50:3596-3604; Liu C-C, et al., Reticulocytes bearing C4d as biomarkers of disease activity for systemic lupus erythematosus. Arthri Rheum. 52:3087-3099, 2005; Navratil J S, et al., Platelet-C4d is highly specific for systemic lupus erythematosus. Arthri Rheum 54:670-674, 2006; and Liu C-C, et al., Lymphocyte-bound complement activation products as biomarkers for diagnosis of systemic lupus erythematosus. Clinical Translational Science, 2: 300-308, 2009].

Levels of C4d and C3d bound to leukocytes, including T lymphocytes, B lymphocytes, monocytes, and granulocytes, were measured using a multicolor flow cytometric assay recently developed, with some modifications. Briefly, peripheral blood leukocytes (PBLs) were prepared by gradient centrifugation using Ficoll Plus (GE Healthcare). After removing contaminating erythrocytes by hypotonic lysis, PBLs were washed with phosphate-buffered saline (PBS), resuspended in PBS containing 1% bovine serum, and aliquoted for antibody staining. Lymphocytes, monocytes, and granulocytes were distinguished based on the expression of characteristic surface molecules and their unique features of forward (size)/side (granularity) scattering. Phycoerythrin- or phycoerythrin Cy5-conjugated mouse monoclonal antibodies (mAb) reactive with lineage-specific cell surface markers (CD3, CD4, and CD8 for T lymphocytes; CD19 for B lymphocytes; BD Biosciences, San Diego, Calif.) were used in conjunction with either anti-human C4d or anti-human C3d mAb (mouse IgG1; reactive with C4d-containing or C3d-containing fragments of C4 or C3; Quidel, San Diego, Calif.) that had been labeled with Alexa Fluor 488 using the Zenon antibody labeling kit (Invitrogen, Carisbad, Calif.).

After staining, cells were analyzed using a FACS Calibur™ flow cytometer and Cell Quest software (Becton Dickinson Immunocytometry Systems). To ensure the specificity of the antibody staining detected, leukocyte aliquots from each patient stained with mouse IgG of appropriate isotypes were routinely included in all experiments. All mAb were used at a concentration of 5 µg/ml. Levels of cell-bound C4d and C3d were expressed as specific median fluorescence intensity (SMFI), which was calculated as the C4d (or C3d)-specific median fluorescence intensity minus the isotype control median fluorescence intensity.

Figure 2:
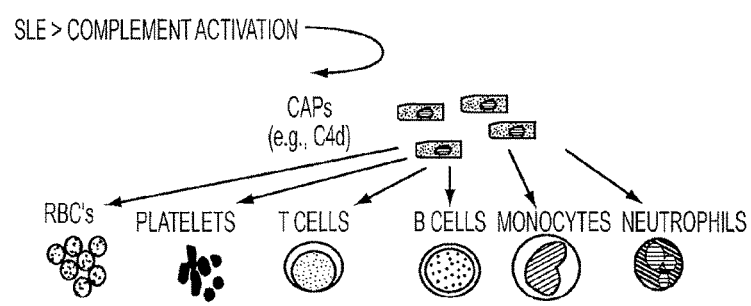
FIG. 2 summarizes a rationale and general approach of CB-CAP profiling and scoring.
Figure 2:
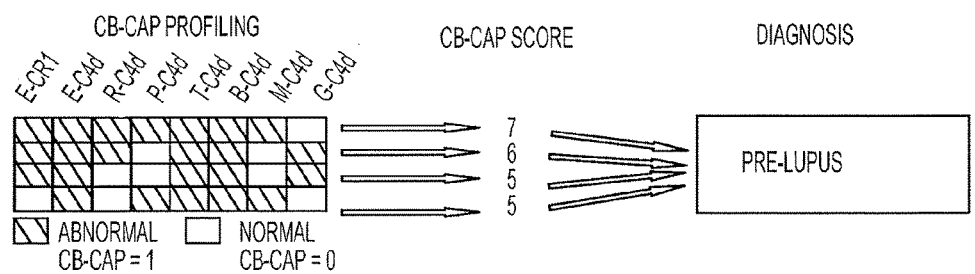

FIG. 2 summarizes a rationale and general approach of CB-CAP profiling and scoring. As shown in FIG. 2, during the stages of Lupus pathogenesis, including the pre-Lupus stage, the complement system is activated and generates complement activation products (CAPs) that can readily bind to cells circulating in the blood. Surface-bound CAPs on peripheral blood cells of a patient can be measured by flow cytometric assays. A CB-CAP profile and a CB-CAP score can be derived for each patient. However, as shown the same CB-CAP score may result from different combinations of elevated CB-CAP levels. Since CAPs may bind to distinct cell types in different patients, it is possible for patients to have the same CB-CAP score but different CB-CAP profiles. Combined with clinical information and/or ACR criteria, the CB-CAP profiles and scores can help the physician to diagnose a patient as exhibiting pre-Lupus.

Statistical Analysis: Distribution normality of continuous data (e.g., age, duration of disease, and CB-CAP levels) was determined using the Shapiro-Wilks test. Depending on the distribution patterns of the data, descriptive statistics, including means, standard deviations, medians, and interquartile range (IQR: $25^{th}$ to $75^{th}$ percentile), were computed. Comparisons of the CB-CAP levels between Lupus patients and healthy controls were performed using two-sample Wilcoxon rank-sum (Mann-Whitney) test. We performed additional analyses with a focus on C4d levels on the 7 circulating cell types (erythrocytes, reticulocytes, platelets, B cells, T cells, granulocytes and monocytes).

For calculating the CB-CAP score, erythrocyte-CR1 and each cell-bound C4d measure was classified in a binary positive (abnormal; score=1) and negative (normal; score=0) fashion. A positive phenotype was assigned when the SMFI of a particular cell type in a patient studied was higher than 2 standard deviation (SD) above the mean SMFI of the respective cell type of the healthy control group. For calculating the score of E-CR1, a positive phenotype was assigned when the SMFI of in a patient studied was lower than 10 (a previously empirically determined level based on the mean level of the healthy control group). Accordingly, the CB-CAP scores (including that of E-CR1) of individual patients may range from 0 to 8. All analyses were performed using the STATA/SE version 11.0 for Window (Stata Corporation, College Station, Tex.).

The study cohort consisted of 447 patients with definite Lupus, 24 patients with pre-Lupus, 286 patients with other immune-inflammatory diseases, and 196 healthy controls. Demographic features of these study groups are summarized in Table 1 below. Although the group of patients with other diseases appeared to be older and consisted of more Caucasians than the other three patient groups, these differences were not statistically different. Comparison of clinical features of patients with definite Lupus or pre-Lupus is shown in Table 2. Unless otherwise specified, data shown were ACR criteria-defined clinical manifestations that had been present at any time point during the course of disease. As defined, patients diagnosed with pre-Lupus had fewer clinical manifestations and laboratory abnormalities (<4) than did patients diagnosed with definite Lupus (>3) (Table 3).

TABLE 1

Demographics of the study cohort

| | Age (Years; mean +/− SD) | Sex (% Female) | Race (% White) |
|---|---|---|---|
| Definite Lupus (n = 447) | 42.1 +/− 13.3 | 92.8 | 80.3 |
| Pre-Lupus (n = 24) | 42.0 +/− 12.3 | 91.7 | 75.0 |
| Other Diseases (n = 286) | 46.1 +/− 15.1 | 86.0 | 90.6 |
| Healthy Controls (n = 196) | 44.9 +/− 13.7 | 90.3 | 83.7 |

TABLE 2

Comparison of Clinical Features of Patients with Definite Lupus versus Pre-Lupus

| | Definite Lupus (%) | Pre-Lupus (%) |
|---|---|---|
| Joints | 90.2 | 54.2 |
| Malar rash | 44.1 | 8.3 |
| Discoid rash | 12.1 | 12.5 |
| Photosensitivity | 58.4 | 12.5 |
| Oral Ulcer | 55.0 | 25 |
| Serositis | 41.8 | 12.5 |
| Neurologic | 10.7 | 0 |
| Renal | 33.3 | 12.5 |
| ANA | 97.3 | 87.5 |
| Serologic | 74.3 | 37.5 |
| Hematologic | 65.1 | 25.0 |
| Anti-dsDNA | 55.9 | 25.0 |
| Anti-Smith | 15.7 | 16.7 |
| Anti-phospholipid | 40.9 | 16.7 |

TABLE 3

ACR Criteria Fulfilled in Patients with Pre-Lupus

| Patient ID | Joints | Malar rash | Discoid rash | Photo-sensitivity | Oral Ulcers | Serositis | Neurologic | Renal | ANA | Serologic | Hematologic | Total ACR Criteria |
|---|---|---|---|---|---|---|---|---|---|---|---|---|
| 101584 | 1 | 0 | 0 | 0 | 0 | 1 | 0 | 0 | 1 | 0 | 0 | 3 |
| 101677 | 0 | 0 | 0 | 0 | 0 | 0 | 0 | 0 | 1 | 1 | 1 | 3 |
| 101924 | 0 | 0 | 0 | 0 | 0 | 0 | 0 | 0 | 1 | 1 | 0 | 2 |
| 102645 | 0 | 0 | 0 | 0 | 1 | 0 | 0 | 0 | 1 | 1 | 0 | 3 |
| 107153 | 0 | 0 | 0 | 0 | 0 | 1 | 0 | 0 | 1 | 0 | 1 | 3 |
| 110738 | 0 | 0 | 0 | 0 | 0 | 1 | 0 | 0 | 1 | 0 | 1 | 3 |
| 110840 | 1 | 0 | 0 | 0 | 0 | 0 | 0 | 0 | 1 | 1 | 0 | 3 |
| 110904 | 0 | 0 | 1 | 1 | 1 | 0 | 0 | 0 | 0 | 0 | 0 | 3 |
| 113007 | 0 | 0 | 0 | 0 | 0 | 0 | 0 | 1 | 1 | 0 | 0 | 2 |
| 125103 | 1 | 1 | 0 | 0 | 0 | 0 | 0 | 0 | 1 | 0 | 0 | 3 |
| 128289 | 1 | 0 | 1 | 1 | 0 | 0 | 0 | 0 | 0 | 0 | 0 | 3 |
| 128390 | 1 | 0 | 0 | 0 | 0 | 0 | 0 | 0 | 1 | 1 | 0 | 3 |
| 128429 | 1 | 0 | 0 | 0 | 0 | 0 | 0 | 0 | 1 | 0 | 0 | 2 |
| 128521 | 1 | 1 | 0 | 0 | 0 | 0 | 0 | 0 | 1 | 0 | 0 | 3 |
| 128627 | 0 | 0 | 0 | 0 | 1 | 0 | 0 | 0 | 1 | 1 | 0 | 3 |
| 130055 | 1 | 0 | 0 | 0 | 1 | 0 | 0 | 0 | 1 | 0 | 0 | 3 |
| 135610 | 1 | 0 | 0 | 0 | 0 | 0 | 0 | 0 | 1 | 1 | 0 | 3 |
| 138922 | 0 | 0 | 0 | 0 | 0 | 0 | 0 | 0 | 1 | 0 | 1 | 2 |
| 145530 | 1 | 0 | 0 | 0 | 0 | 0 | 0 | 0 | 1 | 1 | 0 | 3 |
| 148745 | 0 | 0 | 0 | 1 | 1 | 0 | 0 | 0 | 0 | 0 | 0 | 2 |
| 151528 | 1 | 0 | 1 | 0 | 0 | 0 | 0 | 0 | 1 | 0 | 0 | 3 |
| 151795 | 1 | 0 | 0 | 0 | 0 | 0 | 0 | 1 | 1 | 0 | 0 | 3 |
| 152934 | 1 | 0 | 0 | 0 | 1 | 0 | 0 | 0 | 1 | 0 | 0 | 3 |
| 157292 | 0 | 0 | 0 | 0 | 0 | 0 | 0 | 1 | 1 | 1 | 0 | 3 |

Specific binding of CAPs to circulating blood cells of patients with definite Lupus: A cross-sectional study used flow cytometric assays to measure and compare the levels of CAPs deposited on the surface of circulating blood cells of all study subjects. Consistent with previous studies, significantly elevated levels of C4d and C3d were detected on the surfaces of erythrocytes, reticulocytes, platelets, and lymphocytes of patients with definite Lupus (Tables 4 and 5). Significantly elevated levels of C4d and C3d were also specifically detected on monocytes of patients with definite Lupus (Tables 4 and 5). Consistent with our previous findings, erythrocytes of patients with definite Lupus expressed significantly lower levels of CR1 (E-CR1) than did erythrocytes of patients with other diseases or healthy controls. Interestingly, patients with pre-Lupus, in spite of having fewer than 4 positive ACR classification criteria for definite Lupus, also exhibited decreased E-CR1 and elevated CB-CAP levels on various circulating blood cells that were statistically indistinguishable from those of patients with definite Lupus (Tables 4 and 5). Collectively, these results suggest that increases in CB-CAP levels may precede clinical symptoms and laboratory test abnormalities in patients who may be in the process of developing Lupus despite not yet exhibiting (or being assessed as exhibiting) greater than three ACR criteria, and thus not determined to have definite Lupus.

In general, the levels of cell-bound C4d were significantly higher than those of C3d (Table 4). Therefore, we focused on cell-bound C4d in the CB-CAP profiling and scoring studies described below.

TABLE 4

Comparison of CB-CAPs of Different Study Groups

4A. CB-C4d

| SMFI | E-CR1* | E-C4d* | P-C4d | R-C4d | T-C4d | B-C4d | M-C4d | G-C4d |
|---|---|---|---|---|---|---|---|---|
| Definite Lupus (n = 447) | | | | | | | | |
| Mean | 8.65 | 12.45 | 2.67 | 5.24 | 15.12 | 53.60 | 11.44 | 3.94 |
| Median | 7.93 | 7.57 | 0.71 | 1.47 | 3.70 | 24.90 | 4.83 | 1.49 |
| Maximum | 26.41 | 167.77 | 65.23 | 206.80 | 337.01 | 537.23 | 256.99 | 450.93 |
| Minimum | −0.01 | −1.32 | −2.98 | −0.71 | −1.36 | 1.91 | −0.55 | −0.67 |
| Std Dev | 5.04 | 16.24 | 7.40 | 13.72 | 33.26 | 84.24 | 21.00 | 21.82 |
| Quartile (25%) | 4.84 | 4.72 | 0.15 | 0.75 | 1.57 | 10.69 | 3.07 | 0.85 |
| Quartile (75%) | 11.46 | 13.94 | 1.77 | 3.73 | 12.71 | 55.09 | 9.87 | 2.98 |
| Pre-Lupus (n = 24) | | | | | | | | |
| Mean | 8.62 | 10.54 | 3.95 | 7.14 | 10.99 | 30.41 | 15.15 | 2.88 |
| Median | 8.01 | 10.21 | 1.06 | 2.99 | 4.13 | 26.58 | 6.79 | 1.94 |
| Maximum | 17.40 | 20.06 | 24.23 | 41.17 | 68.22 | 80.05 | 60.40 | 9.30 |
| Minimum | 1.94 | 1.46 | −0.41 | 0.23 | 0.19 | 3.82 | 0.07 | 0.19 |
| Std Dev | 4.29 | 5.22 | 6.74 | 10.36 | 18.32 | 24.55 | 16.97 | 2.70 |
| Quartile (25%) | 6.28 | 6.32 | 0.31 | 0.94 | 1.73 | 10.07 | 3.76 | 1.02 |
| Quartile (75%) | 10.88 | 13.84 | 4.07 | 6.25 | 10.38 | 46.87 | 24.18 | 4.12 |

TABLE 4-continued

Comparison of CB-CAPs of Different Study Groups

Other Diseases (n = 286)

| | | | | | | | | |
|---|---|---|---|---|---|---|---|---|
| Mean | 10.93 | 5.99 | 0.55 | 1.93 | 2.73 | 15.59 | 4.31 | 1.84 |
| Median | 10.43 | 4.48 | 0.40 | 0.88 | 1.52 | 9.84 | 3.35 | 0.99 |
| Maximum | 32.70 | 43.45 | 4.60 | 34.48 | 54.92 | 200.17 | 33.77 | 110.73 |
| Minimum | 0.94 | 0.83 | −1.61 | −0.08 | −0.22 | 0.08 | −0.08 | −1.19 |
| Std Dev | 5.22 | 5.49 | 0.84 | 3.76 | 5.64 | 18.82 | 3.82 | 6.76 |
| Quartile (25%) | 7.11 | 3.16 | 0.08 | 0.51 | 0.89 | 6.95 | 2.06 | 0.52 |
| Quartile (75%) | 14.02 | 6.50 | 0.76 | 1.65 | 2.38 | 16.30 | 5.04 | 1.61 |

Healthy Controls (n = 196)

| | | | | | | | | |
|---|---|---|---|---|---|---|---|---|
| Mean | 12.44 | 4.16 | 0.34 | 1.13 | 1.54 | 9.55 | 4.67 | 1.35 |
| Median | 12.52 | 3.70 | 0.27 | 0.80 | 1.24 | 7.99 | 3.86 | 1.10 |
| Maximum | 28.06 | 12.69 | 3.12 | 7.37 | 6.06 | 38.02 | 19.64 | 7.41 |
| Minimum | 3.07 | 1.07 | −2.66 | −1.37 | −0.42 | 0.49 | 0.00 | −1.10 |
| Std Dev | 5.23 | 2.02 | 0.68 | 1.11 | 1.00 | 6.59 | 3.38 | 1.12 |
| Quartile (25%) | 8.53 | 2.63 | 0.00 | 0.36 | 0.81 | 5.31 | 2.57 | 0.74 |
| Quartile (75%) | 15.54 | 5.22 | 0.58 | 1.55 | 2.19 | 10.84 | 6.13 | 1.64 |
| Cut point (HC Mean + 2 SD) | 10.00 | 8.20 | 1.70 | 3.35 | 3.54 | 22.68 | 11.43 | 3.59 |

4B. CB-C3d

| SMFI | E-C3d* | R-C3d | T-C3d | B-C3d | M-C3d | G-C3d |
|---|---|---|---|---|---|---|

Definite Lupus (n = 447)

| | | | | | | |
|---|---|---|---|---|---|---|
| Mean | 2.38 | 0.94 | 2.51 | 18.78 | 2.13 | 0.91 |
| Median | 0.89 | 0.26 | 1.32 | 15.24 | 1.82 | 0.78 |
| Maximum | 90.76 | 34.23 | 52.97 | 100.98 | 17.29 | 12.95 |
| Minimum | −0.80 | −1.54 | −1.12 | 2.31 | −7.48 | −5.18 |
| Std Dev | 6.26 | 2.86 | 4.19 | 14.07 | 2.24 | 1.09 |
| Quartile (25%) | 0.38 | 0.08 | 0.61 | 9.30 | 0.89 | 0.39 |
| Quartile (75%) | 2.32 | 0.59 | 2.61 | 23.06 | 2.81 | 1.21 |

Pre-Lupus (n = 24)

| | | | | | | |
|---|---|---|---|---|---|---|
| Mean | 1.40 | 1.29 | 1.91 | 22.40 | 2.83 | 0.88 |
| Median | 0.94 | 0.29 | 1.62 | 20.12 | 2.42 | 0.80 |
| Maximum | 4.02 | 8.81 | 6.17 | 55.00 | 10.91 | 2.21 |
| Minimum | −0.01 | 0.02 | −0.46 | 4.50 | −0.49 | −0.47 |
| Std Dev | 1.29 | 2.11 | 1.74 | 15.48 | 2.38 | 0.64 |
| Quartile (25%) | 0.46 | 0.11 | 0.74 | 8.18 | 1.40 | 0.47 |
| Quartile (75%) | 2.57 | 1.95 | 2.28 | 33.56 | 3.39 | 1.34 |

Other Diseases (n = 286)

| | | | | | | |
|---|---|---|---|---|---|---|
| Mean | 0.65 | 0.32 | 1.08 | 15.60 | 1.58 | 0.76 |
| Median | 0.33 | 0.15 | 0.71 | 11.64 | 1.39 | 0.60 |
| Maximum | 12.01 | 14.16 | 15.30 | 77.12 | 11.50 | 22.65 |
| Minimum | −1.98 | −0.81 | −2.04 | −1.59 | −1.56 | −0.93 |
| Std Dev | 1.36 | 1.12 | 1.53 | 12.70 | 1.31 | 1.53 |
| Quartile (25%) | 0.17 | 0.04 | 0.33 | 7.55 | 0.79 | 0.26 |
| Quartile (75%) | 0.62 | 0.26 | 1.36 | 18.32 | 2.21 | 0.99 |

Healthy Controls (n = 196)

| | | | | | | |
|---|---|---|---|---|---|---|
| Mean | 0.29 | 0.09 | 0.83 | 9.94 | 1.69 | 0.69 |
| Median | 0.25 | 0.12 | 0.62 | 8.32 | 1.53 | 0.63 |
| Maximum | 1.55 | 1.13 | 4.03 | 58.72 | 6.97 | 3.19 |
| Minimum | −1.07 | −1.38 | −0.21 | −1.05 | −0.40 | −1.04 |
| Std Dev | 0.31 | 0.27 | 0.68 | 6.44 | 1.14 | 0.60 |
| Quartile (25%) | 0.14 | 0.00 | 0.34 | 5.99 | 0.96 | 0.36 |
| Quartile (75%) | 0.39 | 0.24 | 1.18 | 11.92 | 2.12 | 0.95 |
| Cut point (HC Mean + 2 SD) | 0.91 | 0.63 | 2.19 | 22.82 | 3.97 | 1.89 |

*Specific median fluorescence intensity was shown for all markers except E-CR1, E-C4d, and E-C3d. For these two, specific mean fluorescence intensity was calculated instead.

TABLE 5

Comparison of CB-CAPs in Different Study Groups

5A. CB-C4d

| P value | E-CR1 | E-C4d | P-C4d | R-C4d | T-C4d | B-C4d | M-C4d | G-C4d |
|---|---|---|---|---|---|---|---|---|
| Definite Lupus vs. Pre-Lupus | 0.976 | 0.565 | 0.418 | 0.533 | 0.547 | 0.179 | 0.396 | 0.812 |

TABLE 5-continued

Comparison of CB-CAPs in Different Study Groups

| | | | | | | | | |
|---|---|---|---|---|---|---|---|---|
| Definite Lupus vs. Other Diseases | <0.001 | <0.001 | <0.001 | <0.001 | <0.001 | <0.001 | <0.001 | 0.059 |
| Definite Lupus vs. Healthy Controls | <0.001 | <0.001 | <0.001 | <0.001 | <0.001 | <0.001 | <0.001 | 0.013 |
| Pre-Lupus vs. Other diseases | 0.036 | <0.001 | <0.001 | <0.001 | <0.001 | <0.001 | <0.001 | 0.459 |
| Pre-Lupus vs. Healthy Controls | 0.001 | <0.001 | <0.001 | <0.001 | <0.001 | <0.001 | <0.001 | <0.001 |

5B. CB-C3d

| P value | E-C3d | R-C3d | T-C3d | B-C3d | M-C3d | G-C3d |
|---|---|---|---|---|---|---|
| Definite Lupus vs. Pre-Lupus | 0.443 | 0.577 | 0.488 | 0.221 | 0.135 | 0.909 |
| Definite Lupus vs. Pre-Lupus | <0.001 | <0.001 | <0.001 | 0.002 | <0.001 | 0.148 |
| Definite Lupus vs. Healthy Controls | <0.001 | <0.001 | <0.001 | <0.001 | 0.001 | 0.001 |
| Pre-Lupus vs. Other diseases | 0.010 | <0.001 | 0.012 | 0.014 | <0.001 | 0.691 |
| Pre-Lupus vs. Healthy Controls | <0.001 | <0.001 | <0.001 | <0.001 | <0.001 | 0.1408 |

The results shown above demonstrate that CB-CAPs, particularly C4d, generated during complement activation in patients with definite Lupus or pre-Lupus are capable of binding to a wide range of circulating blood cells. As shown in Table 4, when patients with definite Lupus or pre-Lupus were analyzed as a group, the average levels of C4d bound on the 7 cell types tested were all significantly elevated. However, further analysis of individual patients revealed that elevated C4d levels were not necessarily concurrently present on all cell types in a given patient at a given time (data not shown). When the levels of C4d bound on various cell types in individual patients were meticulously measured at the same study time, it was found that distinct levels of C4d may be detected on a set of cell types in one patient, but on a different set of cell types in another patient (Table 6). Therefore, this kind of select binding of C4d to distinct cell types creates a signature CB-CAP profile unique for each patient. The inventors have thus determined that this information is useful for determining which patients should be considered as exhibiting pre-Lupus.

The present inventors next devised a scoring system utilizing the observed patient-specific CB-CAP profiles. By assigning 1 point for abnormally elevated C4d levels bound on each of the 7 cell types tested (E-C4d, R-C4d, P-C4d, T-C4d, B-C4d, M-C4d, and G-C4d) and for abnormally low level of CR1 expressed by erythrocytes (E-CR1), a CB-CAP score ranging from 0 (no abnormal CB-CAP and CR1 level) to 8 (abnormal CR-1 and CB-CAP levels on all 7 cell types) can be derived for each patient. The cutpoint for abnormal CB-CAP levels for each cell type was defined as the mean CAP level of the respective cell type of the healthy control group plus 2 standard deviations (see Table 4). The cutpoint for abnormal E-CR1 level was empirically determined as SMFI<10 based on our previous study. Using this scoring system, we calculated and compared the CB-CAP scores for each and every patient with definite Lupus, pre-Lupus, or other immune-inflammatory diseases. As shown in Table 7, patients with definite Lupus and pre-Lupus were generally accrued higher CB-CAP scores (with an average score of 2.80 and 4.00, respectively) than did patients with other immune-inflammatory diseases (average score 1.23).

TABLE 6

Differential Binding of CAPs to Distinct Cell Types in Different Patients with Definite Lupus

| Patient ID | E-CR1 | E-C4d | P-C4d | R-C4d | T-C4d | B-C4d | M-C4d | G-C4d | CD4 T-C4d | CD8 T-C4d |
|---|---|---|---|---|---|---|---|---|---|---|
| 111462 | 16.13 | 24.34 | 0.90 | 23.70 | 5.20 | 47.01 | 15.91 | 2.08 | 5.79 | 6.03 |
| 107468 | 7.40 | 5.36 | 6.00 | 11.21 | 148.85 | 88.53 | 124.93 | 0.00 | 76.21 | 255.26 |
| 111271 | 14.87 | 23.38 | 1.67 | 50.82 | 180.73 | 312.06 | 23.55 | 5.00 | 68.56 | 227.63 |
| 101601 | 9.14 | 8.19 | 0.27 | 7.39 | 184.38 | 355.238 | 10.98 | 2.88 | 99.19 | 250.36 |
| 102683 | 22.18 | 7.02 | 1.15 | 7.00 | 129.57 | 180.94 | 16.48 | 2.50 | 234.16 | 0.97 |
| 111521 | 16.80 | 50.83 | 0.36 | 56.30 | 5.84 | 55.86 | 14.49 | 4.21 | 10.62 | 6.25 |
| 111505 | 1.13 | 23.06 | 26.68 | 28.42 | 41.7 | 145 | 197.8 | 40.4 | 31.8 | 54.22 |
| 101658 | 10.49 | 8.33 | 11.42 | 2.46 | 183.62 | 353.52 | 97.17 | 19.43 | 245.61 | 176.94 |
| 94705 | 3.09 | 113.71 | 5.54 | 19.62 | 18.38 | 90.03 | 138.41 | 17.05 | 16.19 | 41.04 |
| 107395 | 4.42 | 44.30 | 69.14 | 40.36 | 404.24 | 174.82 | 778.53 | 343.92 | 376.1 | 411.57 |

TABLE 7

Comparison of the CB-CAP Scores in 3 Different Patient Groups

| | CB-CAP Score | | | | | | | | | Total Score | Average Score |
|---|---|---|---|---|---|---|---|---|---|---|---|
| | 0 (n; %) | 1 (n; %) | 2 (n; %) | 3 (n; %) | 4 (n; %) | 5 (n; %) | 6 (n; %) | 7 (n; %) | 8 (n; %) | | |
| Definite Lupus (total n = 447) | 63; 14 | 101; 24 | 50; 11 | 59; 13 | 44; 10 | 51; 11 | 27; 6 | 29; 6 | 23; 5 | 1250 | 2.80 |
| Pre-Lupus (total n = 24) | 2; 8 | 6; 26 | 2; 8 | 1; 4 | 2; 8 | 2; 8 | 4; 17 | 3; 13 | 2; 8 | 100 | 4.00 |
| Other Diseases (total n = 286) | 114; 38 | 104; 36 | 26; 9 | 14; 5 | 14; 5 | 15; 5 | 2; 1 | 2; 1 | 0; 0 | 352 | 1.23 |

Figure 3:
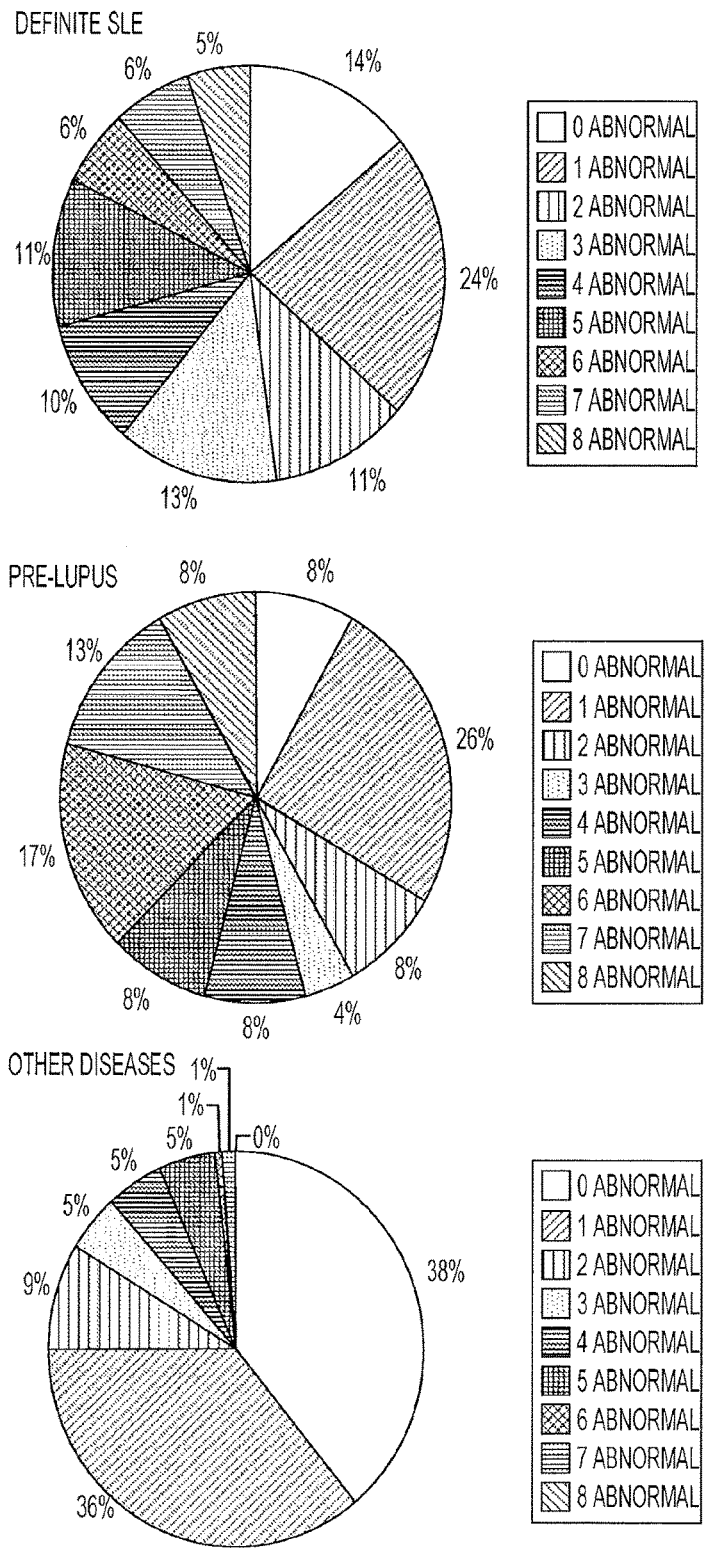
FIG. 3 illustrates the prevalence of patients with different CB-CAP scores within example patient groups.

The prevalence of patients with different CB-CAP scores within each patient group is summarized in FIG. 3. In FIG. 3, it is apparent that high CB-CAP scores were more prevalent in the patient groups of definite Lupus and pre-Lupus than in the patient group of other immune-inflammatory diseases. Remarkably, the frequency distribution of CB-CAP scores among the patient group of pre-Lupus were not significantly different from those of the patients with definite Lupus, but was considerably different from those of patients with other diseases. This finding lends additional support to the determination that the complement-mediated immunopathogenic process may occur insidiously and eventually lead to clinically evident symptoms in a patient. Moreover, binding of CAPs to distinct cell populations in different Lupus patients may indicate unique pathogenic mechanisms in different patients. Together, these results imply that binding of CAPs to circulating cells may indeed be part of the Lupus immunopathogenic process that may continuously evolve and expand. Therefore, the inventors have determined that CB-CAP profiles may serve as surrogate markers of pre-Lupus.

Example 2

The following analyses were performed to determine if CB-CAP assay panels of fewer than 8 assays might perform as well as the full octet.

Study Participants

All study participants were 18 years of age or older and provided written informed consent that was approved by the institutional review board.

Four hundred and twenty-nine patients who met the ACR 1982 or 1997 revised classification criteria for definite SLE (≥4 criteria) were recruited for this study during routine visits to the Lupus Patient Care and Translational Research Center from June 2004 through December 2014. Fifty-one patients who presented SLE-related symptoms but nevertheless did not meet the definite SLE criteria were diagnosed to have pre-lupus.

Two hundred and eighty-five patients with non-SLE immune-inflammatory diseases were recruited during the same period of time. These patients included 41 patients with Sjogren's syndrome, 20 patients with rheumatoid arthritis, 7 patients with scleroderma, 15 patients with antiphospholipid syndrome, 11 patients with idiopathic inflammatory myopathy, 8 patients with vasculitis, 5 patients with inflammatory bowel disease, 4 patients with primary Raynaud's phenomenon, 4 patients with discoid or cutaneous lupus, 3 patients with psoriasis, 3 patients with Wegener's granulomatosis, 1 patient with Bechet's disease, 1 patient with sarcoidosis, 5 patients with various infection, and 191 patients with undifferentiated connective tissue disease or unclear disorders at the time of the visit. In addition, one hundred and ninety-six healthy individuals were recruited as normal controls. To confirm their healthy status, those participants completed a brief questionnaire regarding existing medical conditions.

Flow Cytometric Assays for CB-CAP Profiling

At the time of each participant's visit, a 3-ml sample of blood was collected into a Vacutainer tube containing EDTA as an anticoagulant (Becton Dickinson, Franklin Lakes, N.J.). Blood samples were stored at 4° C. and analyzed within 24 hours after collection. Each blood sample was analyzed for a total of seven CB-CAPs (C4d on 7 cell types—erythrocytes [E-C4d], reticulocytes [R-C4d], T lymphocytes [T-C4d], B lymphocytes [B-C4d], monocytes [M-C4d], and granulocytes [G-C4d], and platelets [P-C4d]), following protocols reported in our recent publications. After staining, cells were analyzed using a FACS Calibur™ flow cytometer and Cell Quest software (Becton Dickinson Immunocytometry Systems). To ensure the specificity of the antibody staining detected, blood cell aliquots from each patient stained with mouse IgG of appropriate isotypes were routinely included in all experiments. All mAb were used at a concentration of 5 µg/ml. Levels of cell-bound C4d were expressed as specific median fluorescence intensity (SMFI), which was calculated as the C4d-specific median fluorescence intensity minus the isotype control median fluorescence intensity.

Scoring of CB-CAP Profiles

For calculating the CB-CAP score, each cell-bound C4d measure was classified in a binary positive (abnormal; score=1) and negative (normal; score=0) fashion. A positive phenotype was assigned when the SMFI of a particular cell type in a patient studied was higher than 2 standard deviation (SD) above the mean SMFI of the respective cell type of the healthy control group. Accordingly, the score of a full spectrum of CB-CAPs (E-C4d/R-C4d/P-C4/T-C4d/B-C4d/M-C4d/G-C4d) in individual patients may range from 0 (minimum) to 7 (maximum). To investigate the capacity of a partial CB-CAP panel in differentiating patients with SLE, pre-lupus, or other autoimmune diseases, one CB-CAP biomarker was removed from the full spectrum at a time and the resultant CB-CAP score was calculated accordingly. For example, G-C4d was excluded from the CB-CAP spectrum during the first pass, resulting in CB-CAP scores ranging from 0 (minimum) to 6 (maximum); M-C4d was excluded in the next pass, resulting in CB-CAP scores ranging from 0 (minimum) to 5 (maximum); and so on.

The above-mentioned CB-CAP scores were calculated based on a binary (normal/abnormal) classification of individual CB-CAP biomarker and did not take into consideration of the actual level of CB-CAP biomarkers (highly abnormal versus modestly abnormal). To compare CB-CAP levels on various circulating cell types among different study populations in a quantitative manner, the level of each CB-CAP biomarker was normalized and scored using a z score system [Kreyszig, E. (1979) Advanced Engineering Methematics ($4^{th}$ Edition)]. A cumulative z score of the full CB-CAP spectrum (seven (7) biomarkers in total) or partial CB-CAP spectrum (2-6 biomarkers) was then calculated by combining the z scores of respective CB-CAP biomarkers.

Statistical Analyses

Distribution normality of CB-CAP scores within each study group was determined using Shapiro-Wilks test. Depending on the distribution patterns of the data, descriptive statistics, including means, standard deviations, medians, and interquartile range (IQR: $25^{th}$ to $75^{th}$ percentile), were computed. The statistical significance of the differences in the CB-CAP scores among patients with definite SLE, patients with pre-lupus, patients with other diseases, and healthy controls were determined using two-sample Wilcoxon rank-sum (Mann-Whitney) test. Utility of cumulative z scores of the full CB-CAP spectrum (7 biomarkers) or partial CB-CAP spectrum (6 biomarkers, 5 biomarkers, 4 biomarkers, 3 biomarkers, or 2 biomarkers) as diagnostic tests for SLE and pre-lupus were assessed using the receiver-operating characteristics (ROC) analysis. All analyses were performed using the STATA/SE version 11.0 for Window (Stata Corporation, College Station, Tex.).

As shown in FIG. 7, studies were performed on 429 patients with Definite SLE, 51 patients with Pre-SLE, 285 patients with Other Diseases (OD) considered to be autoimmune and/or inflammatory, and 196 Healthy Controls. Each individual provided a single blood sample at one random point in time and seven CB-CAP assays (E-C4d, R-C4d, P-C4d, T-C4d, B-C4d, M-C4d, G-C4d) were performed simultaneously on each sample. Medians ($25^{th}$ percentile-$75^{th}$ percentile) were determined for each assay result in each of the four cohorts of subjects. Significant differences, as shown by p values, were observed in comparisons between SLE vs. OD, SLE vs. HC, and Pre-SLE vs. OD. There were no significant differences between SLE and Pre-SLE when comparing E-C4d, R-C4d, P-C4d, M-C4d and G-C4d. However, significant differences were observed between SLE and Pre-SLE when comparing T-C4d and B-C4d. These results indicate that multiple assay panels of CB-CAP assays may serve to identify patients with Pre-SLE as compared with other autoimmune and/or inflammatory diseases, yet determination of B-C4d and T-C4d may serve to distinguish patients with Pre-SLE from those with Definite SLE and thereby be useful in both classification and monitoring an individual who may transition from the Pre-SLE to the Definite SLE stage of disease.

Figure 8:
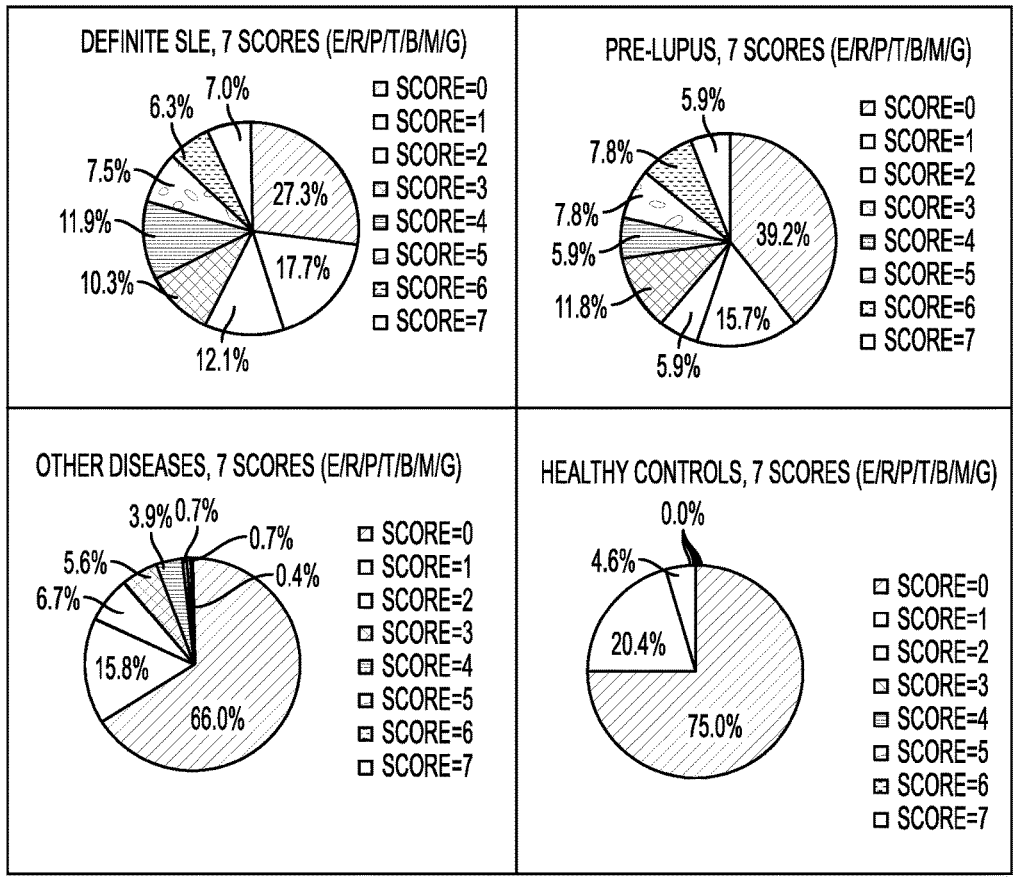
FIG. 8 illustrates the performance of a CB-CAP seven (7) assay panel.

CB-CAP assay results were analyzed in combinations to determine if panels of fewer than 8 assays might serve to distinguish patients with Pre-SLE from those with Other Diseases and from Healthy Controls. Shown in FIGS. 8-13 are the results generated by such analyses as follows:

Panel of 7 CB-CAP Assays: E-C4d, R-C4d, P-C4d, T-C4d, B-C4d, M-C4d, G-C4d (FIG. 8)

Figure 9:
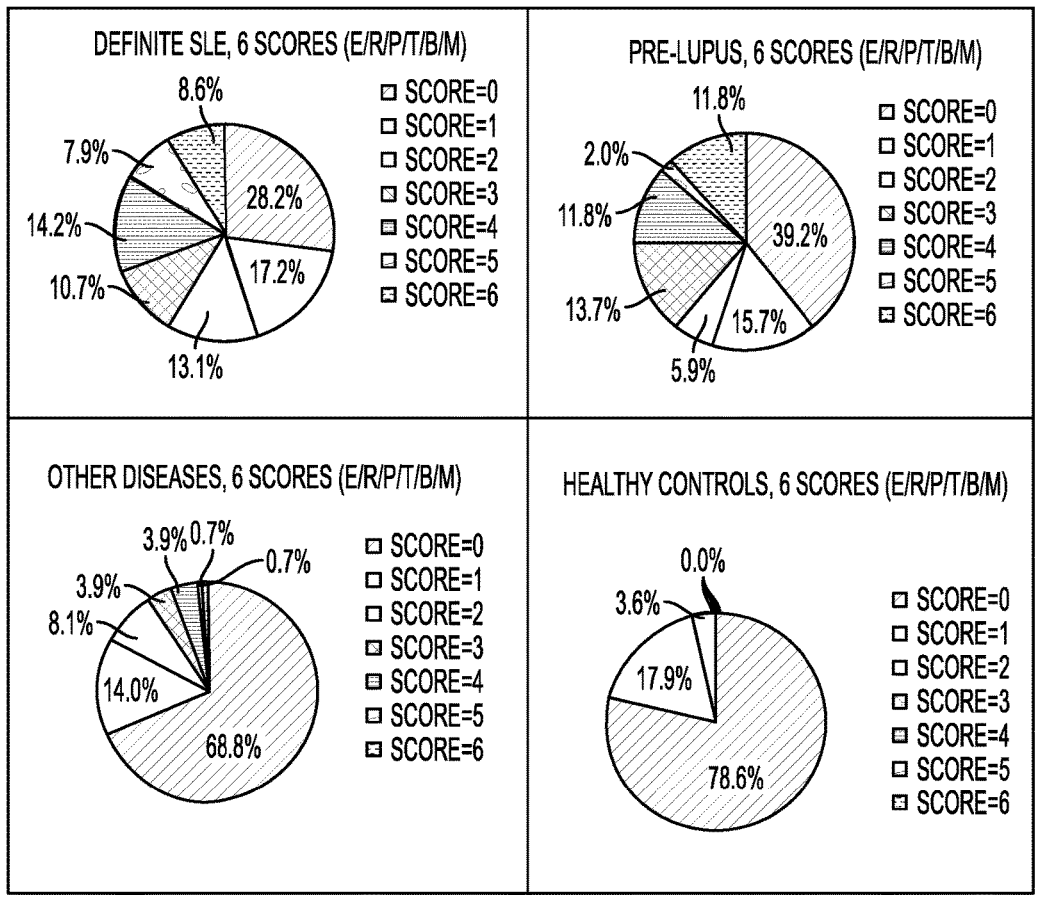
FIG. 9 illustrates the performance of a CB-CAP six (6) assay panel.

Panel of 6 CB-CAP Assays: E-C4d, R-C4d, P-C4d, T-C4d, B-C4d, M-C4d (FIG. 9)

Figure 10:
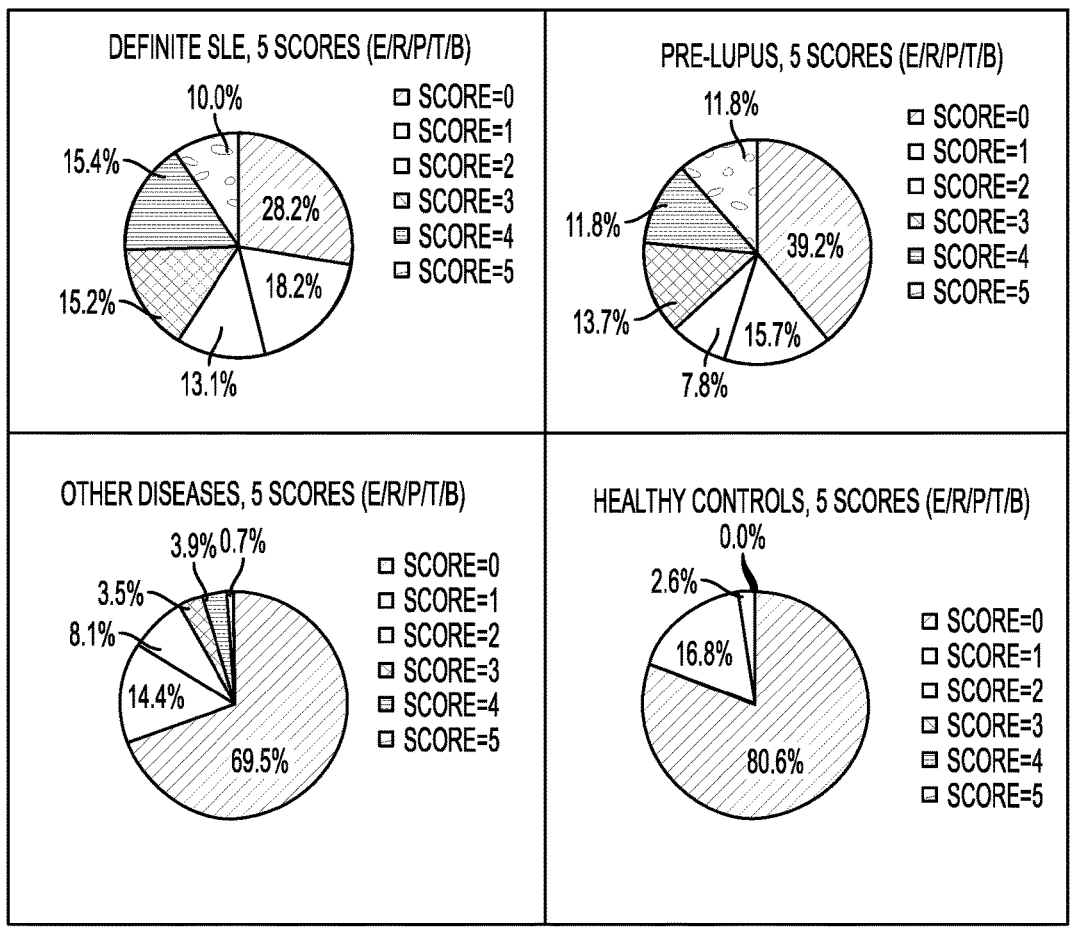
FIG. 10 illustrates the performance of a CB-CAP five (5) assay panel.

Panel of 5 CB-CAP Assays: E-C4d, R-C4d, P-C4d, T-C4d, B-C4d (FIG. 10)

Figure 11:
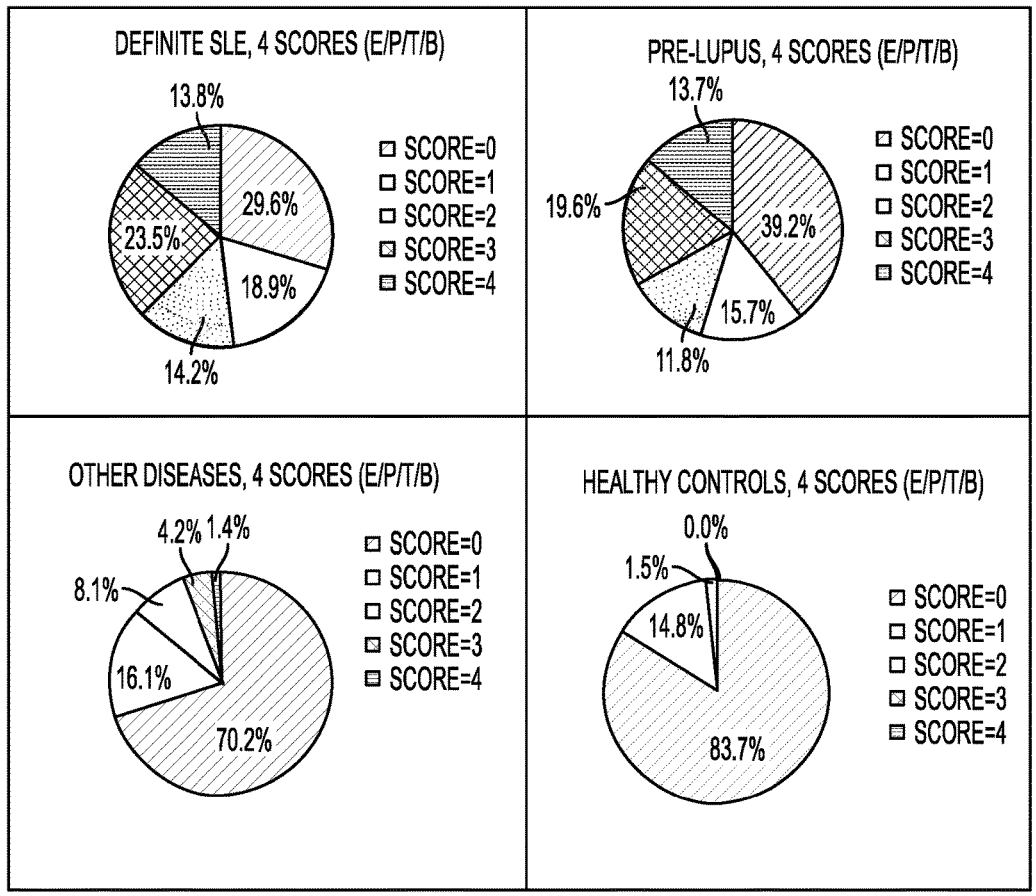
FIG. 11 illustrates the performance of a CB-CAP four (4) assay panel.

Panel of 4 CB-CAP Assays: E-C4d, P-C4d, T-C4d, B-C4d (FIG. 11)

Figure 12:
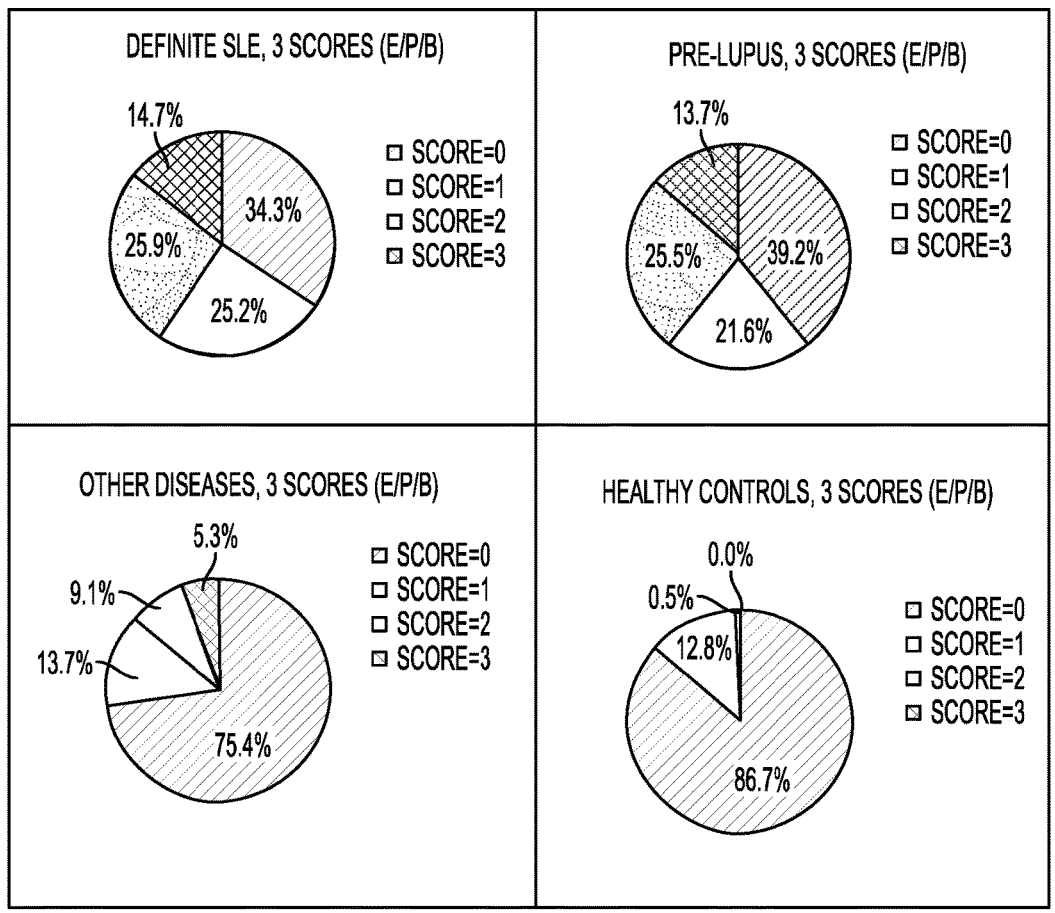
FIG. 12 illustrates the performance of a CB-CAP three (3) assay panel.

Panel of 3 CB-CAP Assays: E-C4d, P-C4d, B-C4d (FIG. 12)

Figure 13:
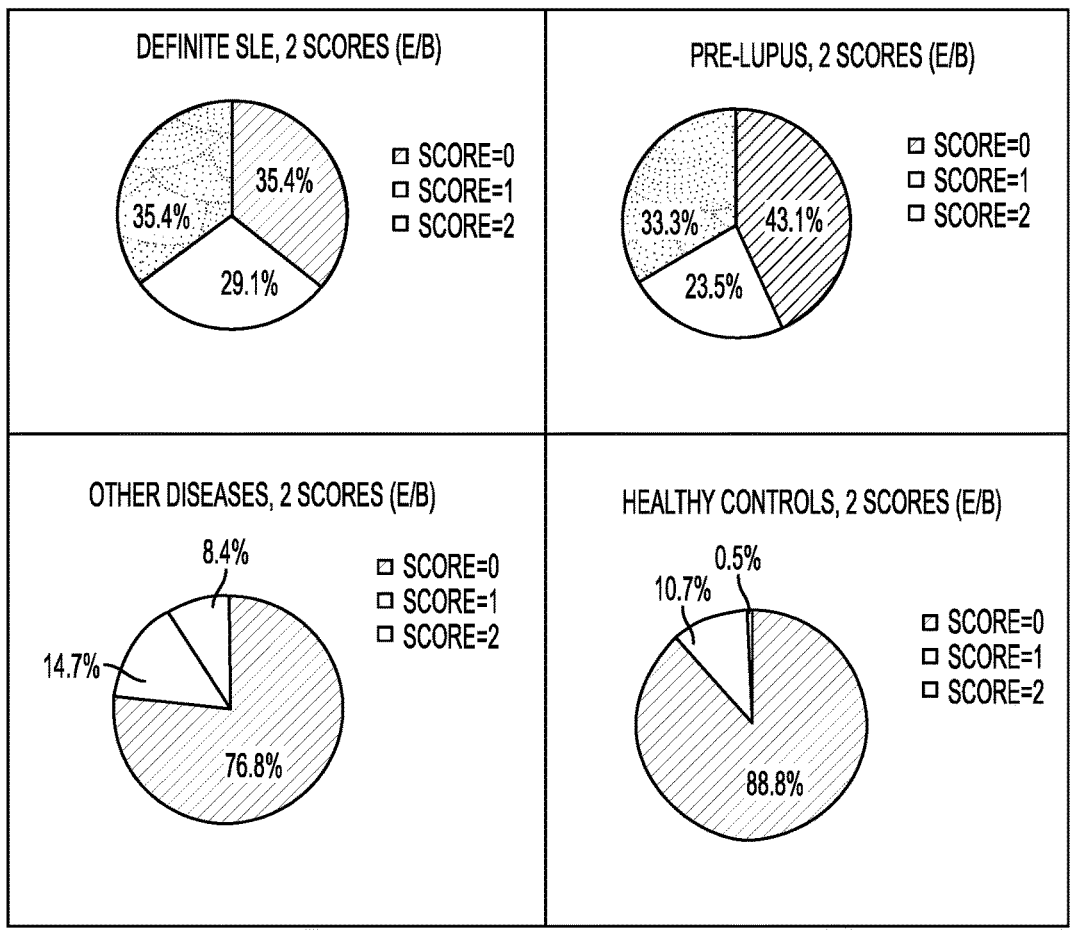
FIG. 13 illustrates the performance of a CB-CAP two (2) assay panel.

Panel of 2 CB-CAP Assays: E-C4d, B-C4d (FIG. 13)

Figure 14A:
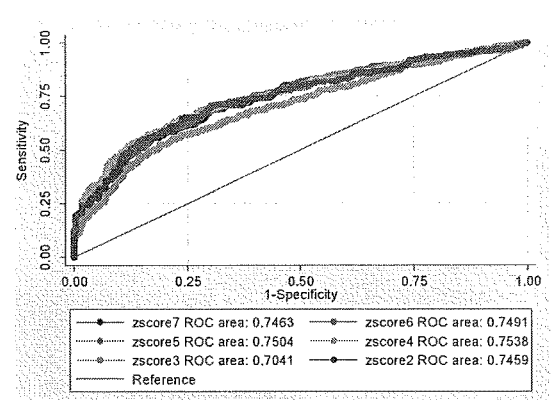
FIGS. 14A-C illustrate z score comparisons of CB-CAP multi-assay panels.
Figure 14B:
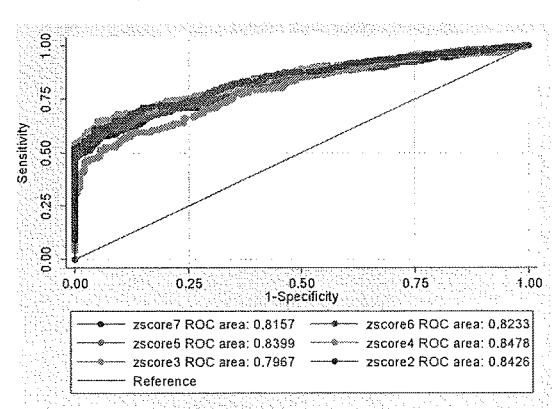
Figure 14C:
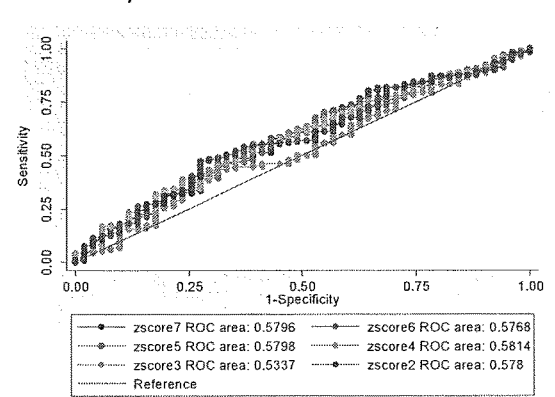

These combinations were determined to be the most significant, whereas other combinations of 2-7 assays were either less significant or non-significant in distinguishing an individual as having Pre-SLE vs. Other Disease. For each blood sample, a "CB-CAP score" was calculated as described above. Statistical analysis comparing CB-CAP scores among the four groups of subjects demonstrates that for every panel of CB-CAP assays (7, 6, 5, 4, 3, and 2 distinct assays in combination), there is no significant difference in the CB-CAP scores when comparing SLE vs. Pre-SLE, yet there is a highly significant difference when comparing SLE and Pre-SLE vs. Other Diseases (p<0.001) and Healthy Controls (p<0.001). Further statistical analyses were performed to calculate z scores and receiver-operating curve (ROC) characteristics. As shown in FIG. 14, for every panel of assays ranging from 7-2 distinct assays, highly significant differences were observed in comparing SLE vs. Other Diseases (AUC 0.70-0.75), and highly significant differences were observed in comparing SLE vs. Healthy Controls (AUC 0.80-0.85), however CB-CAP assay panel results were indistinguishable when comparing SLE vs. Pre-SLE. (AUC 0.53-0.58).

The features and functions described above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

Where features or aspects of the invention are described in terms of a Markush group or other grouping of alternatives, those skilled in the art will recognized that the invention is also thereby described in terms of any individual member or subgroup of members of the Markush group or other group.

Unless indicated to the contrary, all numerical ranges described herein include all combinations and subcombinations of ranges and specific integers encompassed therein. Such ranges are also within the scope of the described invention.

All references cited herein are incorporated by reference herein in their entireties.

We claim:

1. A method of determining whether to classify a patient as exhibiting pre-Lupus, comprising:
   receiving a blood sample for a patient who is determined to meet fewer than four classification criteria for Lupus;
   performing cell-bound complement activation product (CB-CAP) assays on the blood sample to generate a set of blood sampling data for the patient,
      wherein the CB-CAP assays comprise a panel of assays using monoclonal antibodies specifically reactive with at least two of the following CB-CAPs: E-C4d, R-C4d, P-C4d, T-C4d, B-C4d, M-C4d, and G-C4d, and
      wherein the set of blood sampling data comprises levels of at least two of the CB-CAPs for the patient;
   comparing the CB-CAP levels for the patient with a set of normal control levels to determine the CB-CAPs for which the patient's CB-CAP levels are elevated as compared to the control levels;
   generating a score for the patient based upon a number of CB-CAPs for which the patient's CB-CAP levels exceed the control levels by at least a threshold amount;

determining whether the patient's score is greater than an average score for other subjects, exhibiting immune and/or inflammatory diseases that are not Lupus or pre-Lupus; and if the patient's score is determined to be greater than the average score for the other subjects, classifying the patient as exhibiting an increased risk of developing Lupus.

2. The method of claim 1, wherein the CB-CAP levels comprise levels for each of E-C4d and B-C4d.

3. The method of claim 1, wherein the CB-CAP levels comprise levels for each of E-C4d, P-C4d and B-C4d.

4. The method of claim 1, wherein the CB-CAP levels comprise levels for each of E-C4d, P-C4d, T-C4d and B-C4d.

5. The method of claim 1, wherein the CB-CAP levels comprise levels for each of E-C4d, R-C4d, P-C4d, T-C4d and B-C4d.

6. The method of claim 1, wherein the CB-CAP levels comprise levels for each of E-C4d, R-C4d, P-C4d, T-C4d, B-C4d and M-C4d.

7. The method of claim 1, wherein the CB-CAP levels comprise levels for each of E-C4d, R-C4d, P-C4d, T-C4d, B-C4d, M-C4d, and G-C4d.

8. The method of claim 1, further comprising:

for a plurality of cell lineages and/or lineage subsets, determining whether a level of cells in each of the lineages and/or lineage subsets in the blood sample exceeds a threshold percentage of cells in the sample; and when performing the CB-CAP assays, performing the CB-CAP assays only on CB-CAPs corresponding to lineages and/or lineage subsets having a level of cells that exceeds the threshold, and not performing the CB-CAP assays on CB-CAPs corresponding to lineages and/or lineage subsets having a level of cells that does not exceed the threshold.

* * * * *